(12) United States Patent
Reed et al.

(10) Patent No.: US 6,545,128 B1
(45) Date of Patent: Apr. 8, 2003

(54) ANTI-BAX INHIBITOR PROTEIN ANTIBODIES

(75) Inventors: John C. Reed, Rancho Santa Fe, CA (US); Qunli Xu, La Jolla, CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 09/611,175

(22) Filed: Jul. 6, 2000

Related U.S. Application Data

(62) Division of application No. 09/115,934, filed on Jul. 15, 1998, now Pat. No. 6,130,317, which is a continuation of application No. 08/818,514, filed on Mar. 14, 1997, now Pat. No. 5,837,838.

(51) Int. Cl.[7] .................. A61K 39/395; G01N 33/53; C07K 16/00
(52) U.S. Cl. ................. 530/387.1; 530/300; 530/350; 530/388.2; 530/386; 530/388.1; 424/139.1; 424/141.1; 424/148.1; 424/154.1; 424/172.1; 424/145.1; 435/7.1; 435/332
(58) Field of Search ................ 424/139.1, 141.1, 424/148.1, 154.1, 172.1, 145.1; 435/7.1, 332; 530/300, 350, 387.1, 386, 388.1, 388.2

(56) References Cited

U.S. PATENT DOCUMENTS 5,506,344 A  4/1996  Tsujimoto et al. ..... 530/388.85

OTHER PUBLICATIONS

GenBank accession N28421.
GenBank accession X75861.
Reddy et al., "The cloning and characterization of a maternally expressed novel zinc finger nuclear phosphoprotein (xnf7) in *Xenopus laevis*," *Developmental Biology* 148:107–116 (1991).
Tissot et al., "Molecular cloning of a new interferon–induced factor that represses human immunodeficiency virus type 1 long terminal repeat expression," *Journal of Biological Chemistry* 270:14891–14898 (1995).
Tsugu et al., "The location of a disease–associated polymorphism and genomic structure of the human 52–kDa Ro/SSA locus (SSA1)," *Genomics* 24:541–548 (1994).
Walter et al., "Identification of a Novel Conserved Human Gene, TEGT," *Genomics* 28:301–304 (1995).
Walter et al., "A novel, conserved gene of the rat that is developmentally regulated in the testis," *Mammalian Genome* 5:216–221 (1994).
Xu and Reed, "A yeast genetics approach to cloning Bax-–suppressors," *Proceedings of the Am. Assoc. for Cancer Res.* 38:344 (1997).

*Primary Examiner*—Yvonne Eyler
*Assistant Examiner*—Nirmal S Basi
(74) *Attorney, Agent, or Firm*—Campbell & Flores LLP

(57) ABSTRACT

The present invention provides substantially purified nucleic acid molecules encoding Bax inhibitor protein-1 (BI-1; SEQ ID NO: 1) or Bax inhibitor protein-2 (BI-2; SEQ ID NO: 4), nucleic acid molecules complementary thereto (SEQ ID NO: 2 and SEQ ID NO: 5, respectively), portions of such nucleic acid molecules, vectors containing the nucleic acid molecules, and host cells containing the vectors. The invention also provides methods of using such nucleic acid molecules to identify the presence of a nucleic acid molecule encoding a Bax inhibitor protein in a sample or to increase or decrease the level of expression of a Bax inhibitor protein in a cell. In addition, the invention provides substantially purified BI-1 (SEQ ID NO: 3) and BI-2 (SEQ ID NO: 6) polypeptides, portions of such polypeptides, and antibodies specific for BI-1 or BI-2. The invention also provides methods of using a BI-1 or BI-2 polypeptide, or a peptide portion thereof, to identify the presence of a member of the Bcl-2 family of proteins in a sample. The invention further provides methods of identifying agents that can modulate the binding of BI-1 or BI-2 to a Bcl-2 family protein, or that can modulate the function of BI-1 or BI-2, irrespective of its ability to bind a Bcl-2 family protein.

10 Claims, 1 Drawing Sheet

```
MNIFDRKINF DALLKFSHIT PSTQQHLKKV YASFALCMFV AAAGAYVHMV    50
THFIQAGLLS ALGSLILMIW LMATPHSHET EQKKLGLLAG FAFLTGIGLG   100
PALEFCIAVN PSILPTAFMG TAMIFTCFTL SALYARRRSY LFLGGILMSA   150
LSLLLLSSLG NVFFGSIWLF QANLYVGLVV MCGFVLFDTQ LIIEKAEHGD   200
QDYIWHCIDL FLDFITVFRK LMMILAMNEK DKKKEKK                 237
```

FIG. 1

```
MEEPQKSYVN TMDLERDEPL KSTGPQISVS EFSCHCCYDI LVNPTTLNCG    50
HSFCRHCLAL WWASSKKTEC PECREKWEGF PKVSILLRDA IEKLFPDAIR   100
LRFEDIQQNN DIVQSLAAFQ KYGNDQIPLA PNTGRANQQM GGGFFSGVLT   150
ALTGVAVVLL VYHWSSRESE HDLLVHKAVA KWTAEEVVLW LEQLGPWASL   200
YRERFLSERV NGRLLLTLTE EEFSKTPYTI ENSSHRRAIL MELERVKALG   250
VKPPQNLWEY KAVNPGRSLF LLYALKSSPR LSLLYLYLFD YTDTFLPFIH   300
TICPLQEDSS GEDIVTKLLD LKEPTWKQWR EFLVKYSFLP YQLIAEFAWD   350
WLEVHYWTSR FLIINAMLLS VLELFSFWRI WSRSELKTVP QRMWSHFWKV   400
STQGLFVAMF WPLIPQFVCN CLFYWALYFN PIINIDLVVK ELRRLETQVL   450
```

ANTI-BAX INHIBITOR PROTEIN ANTIBODIES

This application is a divisional of application Serial No. 09/115,934, filed Jul. 15, 1998, now U.S. Pat. No. 6,130,317, issued Oct. 10, 2000, which is a continuation of application Serial No. 08/818,514, filed Mar. 14, 1997, now U.S. Pat. No. 5,837,838, issued Nov. 17, 1998.

This invention was made with government support under grant number RP951168 awarded by the United States Department of Defense and grant number DAMD17-96-1-6210 awarded by the United States Army. The government has certain rights in the invention.

BACKGROUND OF THE INVENTION

FIELD OF THE INVENTION

The present invention relates generally to molecular biology and the regulation of cell death and, more specifically, to proteins that modulate the function of the Bax protein, which is involved in inducing apoptosis.

BACKGROUND INFORMATION

In essentially all self-renewing tissues, a balance is struck between cell production by mitogenesis and cell loss due to programmed cell death, thereby maintaining total cell numbers within a physiologically appropriate range. In pathological conditions, however, the balance in cell production and cell loss can be disrupted. In cancer, for example, an increased amount of cell production due to a shortened cell cycle time or a decreased amount of cell death due to dysregulation of a programmed cell death pathway results in the growth of a tumor.

With regard to programmed cell death, a variety of stimuli, which generally occur external to the cell, initiate a pathway that ultimately results in apoptosis of the cell. As is common for most signal transduction pathways, the various different stimuli that induce apoptosis likely initiate the process of programmed cell death through specific pathways. However, most if not all of these initial pathways converge at a common point that generally involves a member of the Bcl-2 family of proteins.

The Bcl-2 family of proteins regulate a distal step in the evolutionarily conserved pathway for programmed cell death and apoptosis, with some members of this family functioning as suppressors of cell death (anti-apoptotic proteins) and other members functioning as promoters of cell death (pro-apoptotic proteins). Overexpression of the anti-apoptotic protein, Bcl-2, for example, blocks neuronal cell death that otherwise is induced in vitro by various stimuli, including neurotrophic factor withdrawal, various oxidants, glucose deprivation, certain neurotrophic viruses, and amyloid β-peptide. In addition, Bcl-2 is overexpressed in some tumor cells and, in part, may contribute to tumor growth by altering the balance between cell division and cell death.

In comparison, overexpression of the pro-apoptotic protein, Bax, for example, promotes cell death when triggered by a variety of inducers of apoptosis, including growth factor withdrawal, ionizing radiation, and anti-Fas antibody. In addition, elevations in Bax expression occur in association with cell death induced by a variety of stimuli, including neuronal cell death that occurs due to ischemia, epilepsy, spinal cord injury, and certain neurodegenerative diseases such as Parkinson's disease and Alzheimer's disease.

Although aberrant expression of members of the Bcl-2 family of proteins is associated with various pathologic conditions, the mechanisms by which these proteins mediate their action is not known. Often, the action of a protein can be inferred from its structural relationship to other proteins, whose functions are known. However, while the Bcl-2 family proteins share certain structural homologies with each other, they do not share substantial amino acid sequence homology with other proteins, further hindering attempts to understand how the Bcl-2 family proteins such as Bcl-2 and Bax regulate cell death. Thus, a need exists to identify proteins involved in the programmed cell death pathway. The present invention satisfies this need and provides related advantages as well.

SUMMARY OF THE INVENTION

The present invention provides substantially purified nucleic acid molecules encoding Bax inhibitor proteins, including Bax inhibitor protein-1 (BI-1) and Bax inhibitor protein-2 (BI-2), nucleic acid molecules complementary thereto, portions of such nucleic acid molecules, vectors containing the nucleic acid molecules, and host cells containing the vectors. For example, the invention provides a nucleotide sequence encoding BI-1 (SEQ ID NO: 1) and a nucleotide sequence encoding BI-2 (SEQ ID NO: 4), as well as nucleotide sequences complementary thereto (SEQ ID NO: 2 and SEQ ID NO: 5, respectively).

The invention also provides methods of using nucleic acid molecules encoding Bax inhibitor proteins. Such nucleic acid molecules can be used, for example, as probes to identify the presence of a nucleic acid molecule encoding a Bax inhibitor protein in a sample. A nucleic acid molecule of the invention also can be used to increase the level of expression of a Bax inhibitor protein in a cell by introducing the nucleic acid molecule into the cell under conditions that allow for expression of the encoded Bax inhibitor protein. A nucleic acid molecule of the invention also can be used to decrease the level of expression of a Bax inhibitor protein in a cell by introducing the nucleic acid molecule into the cell under conditions that allow for expression of the molecule in an antisense orientation, such that the antisense molecule can bind to a nucleic acid encoding the Bax inhibitor protein in the cell. By increasing or decreasing the expression of a Bax inhibitor protein in a cell, the likelihood that the cell will undergo apoptosis can be increased or decreased The invention also provides substantially purified Bax inhibitor proteins. For example, the invention provides a BI-1 polypeptide having the amino acid sequence of SEQ ID NO: 3 (FIG. 1) and a BI-2 polypeptide having the amino acid sequence of SEQ ID NO: 6 (FIG. 2). The invention also provides portions of such polypeptides, which can be useful, for example, for raising antibodies specific for a Bax inhibitor protein. Accordingly, the invention provides antibodies specific for a Bax inhibitor protein such as BI-1 or BI-2.

The invention also provides methods of using a BI-1 or BI-2 polypeptide, or a peptide portion thereof, to identify the presence of other Bax inhibitor proteins or of a member of the Bcl-2 family of proteins in a sample. Such a method is based on the present disclosure that a Bax inhibitor protein can form homodimers and, in addition, can specifically associate with a member of the Bcl-2 family of proteins such as Bcl-2 or Bax to form a heterodimer.

The invention further provides methods of identifying agents that can modulate the formation of Bax inhibitor protein homodimers or that modulate the binding of a Bax inhibitor protein to a member of the Bcl-2 family of proteins. Such a method is useful, for example, for screening large libraries of molecules to identify those agents that can increase or decrease homodimer or heterodimer formation and, therefore, are most likely to be useful as drugs for treating pathologies characterized by aberrant levels of apoptosis.

BRIEF DESCRIPTION OF THE DRAWINGS

FIG. 1 shows the amino acid sequence for BI-1 (SEQ ID NO: 3), as deduced from SEQ ID NO: 1. Underlining indicates six putative transmembrane domains.

FIG. 2 shows the amino acid sequence for BI-2 (SEQ ID NO: 6), as deduced from SEQ ID NO: 4. A "RING finger" motif is shown in bold print. Underlining indicates two putative transmembrane domains.

DETAILED DESCRIPTION OF THE INVENTION

The present invention provides substantially purified nucleic acid molecules encoding Bax inhibitor proteins, including Bax inhibitor protein-1 (BI-1) and Bax inhibitor protein-2 (BI-2). For example, the invention provides a nucleotide sequence encoding BI-1 (SEQ ID NO: 1) and a nucleotide sequence encoding BI-2 (SEQ ID NO: 4).

As used herein, the term "substantially purified," when used in reference to a nucleic acid molecule of the invention, means that the nucleic acid molecule is relatively free from contaminating lipids, proteins, nucleic acids or other cellular material normally associated with a nucleic acid molecule in a cell. A substantially purified nucleic acid molecule encoding a Bax inhibitor protein such as BI-1 or BI-2 can be obtained, for example, by chemical synthesis of the nucleotide sequence shown as SEQ ID NO: 1 or SEQ ID NO: 4, respectively, or by cloning the molecule using a method such as that disclosed in Example I.

As disclosed herein, the Bax inhibitor proteins, BI-1 and BI-2, were identified based on their ability to suppress Bax-induced cell death in yeast cells genetically modified to express a mammalian Bax protein and, thus, were named Bax inhibitor proteins (see Example II). However, the action of a Bax inhibitor protein is, in fact, cell type specific and, in some cases, expression of a Bax inhibitor protein in a cell can increase the likelihood that the cell will undergo apoptosis (compare Example III.A. and Example III.B.). Thus, it should be understood that the action of a Bax inhibitor protein is cell specific, due, for-example, to the members of the Bcl-2 family of proteins normally expressed in a particular cell type and the relative amounts of each member with respect to each other and, therefore, that a Bax inhibitor protein acts to modulate Bax activity.

As used herein, the term "member of the Bcl-2 family of proteins" or "Bcl-2 family proteins" means 1) those antiapoptotic proteins that contains one of the following Bcl-2 domains, BH-1, BH-2, BH-3 or BH-4, and that, upon expression in a cell, suppress cell death, and 2) those pro-apoptotic proteins that contain one of the Bcl-2 domains and that, upon expression in a cell, promote cell death (Zha et al., *J. Biol. Chem.* 271:7440–7444 (1996), which is incorporated herein by reference). The term "anti-apoptotic protein" is used herein to refer to a member of the Bcl-2 family of proteins ("Bcl-2 family proteins"), the expression of which in a cell is associated with a suppression of programmed cell death (apoptosis). Bcl-2, Bcl-$X_L$, Bcl-w, A1, Afl-1, Nr13, CED-9, E1b (19 kDa), BHRF-1 and Mcl-1 are examples of anti-apoptotic proteins, since the expression of one or more of these proteins in a cell is associated with a suppression of apoptosis in the cell upon exposure to conditions that otherwise would result in apoptosis. The term "pro-apoptotic protein" is used herein to refer to a member of the Bcl-2 family of proteins, the expression of which in a cell is associated with the induction of apoptosis. Bax, Bak, Bad, Bik, Bid and Bcl-$X_S$ are examples of pro-apoptotic proteins, since the expression of one or more of these proteins in a cell is associated with the occurrence of apoptosis.

As used herein, the term "suppress," when used in reference to apoptosis, means that the likelihood that apoptosis will occur has been reduced. For example, expression of Bcl-2 in a cell reduces the likelihood that the cell will undergo apoptosis in response to a stimulus that otherwise would induce apoptosis in the cell. As disclosed herein, expression of a Bax inhibitor protein in a cell can suppress Bax-induced cell death, where, in the absence of such Bax inhibitor protein expression, Bax induces apoptosis. It should be recognized that the likelihood that a cell will undergo apoptosis is based on examination of a population of cells. Thus, while reference is made to suppression of apoptosis of a cell, such a determination is made by observing the level of apoptosis of a population of cells, which can be a cloned population of cells (see Examples II and III).

A nucleic acid molecule of the invention is exemplified by the nucleotide sequence shown as SEQ ID NO: 1, which encodes a BI-1 polypeptide (SEQ ID NO: 3; FIG. 1), and by the nucleotide sequence shown as SEQ ID NO: 4, which encodes a BI-2 polypeptide (SEQ ID NO: 6; FIG. 2). The cDNA encoding BI-1 is very similar, but not identical, to a previously cloned cDNA named TEGT (Walter et al., *Genomics* 28:301–304 (1995), which is incorporated herein by reference; GenBank Accession #X75861), each of which is incorporated herein by reference). For example, as compared to TEGT, the nucleotide sequence encoding BI-1 (SEQ ID NO: 1) contains an additional 33 nucleotides at the 5'-end, including an in-frame stop codon upstream of the predicted open reading frame (ORF; Example I.A.).

Due to the degeneracy of the genetic code, and in view of the disclosed amino acid sequences of BI-1 (SEQ ID NO: 3) and BI-2 (SEQ ID NO: 6), additional nucleic acid molecules of the invention would be well known to those skilled in the art. Such nucleic acid molecules have a nucleotide sequence that is different from SEQ ID NO: 1 or SEQ ID NO: 4 but, nevertheless, encode the amino acid sequence shown as SEQ ID NO: 3 or SEQ ID NO: 6, respectively. Thus, the invention provides nucleic acid molecules comprising nucleotide sequences encoding the amino acid sequence of BI-1 (SEQ ID NO: 3) and nucleic acid molecules comprising nucleotide sequences encoding the amino acid sequence of BI-2 (SEQ ID NO: 6).

As used herein, reference to "a nucleic acid molecule encoding" a Bax inhibitor protein indicates 1) the polynucleotide sequence of one strand of a double stranded DNA molecule comprising the nucleotide sequence that codes, for example, for BI-1 or for BI-2 and can be transcribed into an RNA that encodes the polypeptide, or 2) an RNA molecule, which can be translated into a polypeptide. SEQ ID NO: 1 and SEQ ID NO: 4 are examples of nucleic acid molecules encoding a Bax inhibitor protein.

It is recognized that a double stranded DNA molecule also comprises a second polynucleotide strand, which is complementary to the coding strand, and that the disclosure of a polynucleotide sequence comprising a coding sequence necessarily discloses the complementary polynucleotide sequence. Accordingly, the invention provides polynucleotide sequences, including, for example, polydeoxyribonucleotide or polyribonucleotide sequences that are complementary 1) to the nucleotide sequence shown as SEQ ID NO: 1 (see SEQ ID NO: 2); 2) to a nucleic acid molecule encoding a BI-1 polypeptide having the amino acid sequence shown as SEQ ID NO: 3; 3) to the nucleotide sequence shown as SEQ ID NO: 4 (see SEQ ID NO: 5); and 4) to a nucleic acid molecule encoding a BI-2 polypeptide having the amino acid sequence shown as SEQ ID NO: 6.

As used herein, the term "polynucleotide" is used in its broadest sense to mean two or more nucleotides or nucleotide analogs linked by a covalent bond. The term "oligonucleotiden" also is used herein to mean two or more nucleotides or nucleotide analogs linked by a covalent bond, although those in the art will recognize that oligonucleotides generally are less than about fifty to about one hundred nucleotides in length and, therefore, are a subset within the broader meaning of the term "polynucleotide."

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can comprise nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997)). The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977–986 (1994); Ecker and Crooke, *BioTechnology* 13:351360 (1995)).

Where it is desired to synthesize a polynucleotide of the invention, the artisan will know that the selection of particular nucleotides or nucleotide analogs and the covalent bond used to link the nucleotides will depend, in part, on the purpose for which the polynucleotide is prepared. For example, where a polynucleotide will be exposed to an environment containing substantial nuclease activity, the artisan will select nucleotide analogs or covalent bonds that are relatively resistant to the nucleases. A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs and, therefore, can be used to produce such a polynucleotide recombinantly from an appropriate template (see Jellinek et al., supra, 1995).

The invention also provides nucleotide sequences that can bind to a nucleic acid molecule of the invention. Such nucleotide sequences are useful, for example, as polymerase chain reaction (PCR) primers or probes, which can hybridize to a nucleic acid molecule encoding a Bax inhibitor protein and allow the identification of such a nucleic acid molecule, or of a sequence complementary thereto, in a sample. A nucleotide sequence of the invention is characterized, in part, in that it is at least nine nucleotides in length, such sequences being particularly useful as primers for PCR, and can be at least fourteen nucleotides in length or, if desired, at least seventeen nucleotides in length, such nucleotide sequences being particularly useful as hybridization probes, although these sequences also can be used as primers for PCR.

The invention also provides antisense nucleic acid molecules, which are complementary to a nucleic acid molecule encoding a Bax inhibitor protein and can bind to and inhibit the expression of the nucleic acid molecule. An antisense molecule can be complementary to all or a portion of the nucleotide sequences shown as SEQ ID NO: 1, which encodes BI-1, and, therefore, can consist of all or a portion of SEQ ID NO: 2, or can be complementary to all or a portion of SEQ ID NO: 4, which encodes BI-2, and, therefore, can consist of all or a portion of SEQ ID NO: 5. Such antisense nucleic acid molecules are useful, for example, for decreasing the expression of BI-1 or BI-2, respectively, in a cell, thereby abrogating the suppression of Bax in the cell.

Antisense methods involve introducing the nucleic acid molecule, which is complementary to and can hybridize to the target nucleic acid molecule, into a cell. An antisense nucleic acid molecule can be a chemically synthesized polynucleotide, which can be introduced into the target cells by methods of transfection, or can be expressed from a plasmid or viral vector, which can be introduced into the cell and stably or transiently expressed using well known methods (see, for example, Sambrook et al., *Molecular Cloning: A laboratory manual* (Cold Spring Harbor Laboratory Press 1989); Ausubel et al., *Current Protocols in Molecular Biology* (Green Publ., N.Y. 1989), each of which is incorporated herein by reference). Such methods, including methods of synthesizing a nucleic acid molecule and the use of vectors or other means for introducing a nucleic acid molecule into a cell, similarly can be used to introduce a nucleic acid encoding a Bax inhibitor protein into a cell.

One in the art would know that the ability of an antisense nucleic acid molecule to hybridize to a target nucleic acid sequence depends, for example, on the degree of complementarity shared between the sequences, the GC content of the hybridizing molecules, and the length of the antisense nucleic acid sequence, which is at least nine nucleotides in length, generally at least thirty nucleotides in length or at least fifty nucleotides in length, and can be up to the full length of a target nucleotide sequence, which encodes a Bax inhibitor protein (see Sambrook et al., "Molecular Cloning: A laboratory manual (Cold Spring Harbor Laboratory Press 1989), which is incorporated herein by reference). Thus, an antisense molecule of the invention comprises at least nine contiguous nucleotides of SEQ ID NO: 2 or SEQ ID NO: 5.

An antisense molecule is selected, in part, based on its specificity for a target molecule, which is a nucleic acid molecule encoding a Bax inhibitor protein. Accordingly, it is recognized that a step in identifying a antisense nucleic acid molecule of the invention is the determination, for example, by searching a database, that the selected sequence is specific for the target nucleic acid molecule, but does not share substantial homology with an unrelated sequence such that the antisense molecule would cross-hybridize to and inactivate expression of the unrelated sequence. Such a determination similarly is made where a nucleotide sequence is selected for use as a PCR primer or as a hybridization probe.

The invention also provides vectors comprising a nucleic acid molecule of the invention and host cells, which are appropriate for maintaining such vectors. Vectors, which can be cloning vectors or expression vectors, are well known in the art and commercially available. An expression vector comprising a nucleic acid molecule of the invention, which can encode a Bax inhibitor protein or can be an antisense molecule, can be used to express the nucleic acid molecule in a cell.

In general, an expression vector contains the expression elements necessary to achieve, for example, sustained transcription of the nucleic acid molecule, although such elements also can be inherent to the nucleic acid molecule cloned into the vector. In particular, an expression vector contains or encodes a promoter sequence, which can provide constitutive or, if desired, inducible expression of a cloned nucleic acid sequence, a poly-A recognition sequence, and a ribosome recognition site, and can contain other regulatory elements such as an enhancer, which can be tissue specific. The vector also contains elements required for replication in a procaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, D. V. Goeddel, ed. (Academic Press, Inc., 1990); Jolly, Canc. Gene Ther. 1:51–64 (1994); Flotte, J. Bioenerg. Biomemb. 25:37–42 (1993); Kirshenbaum et al., J. Clin. Invest 92:381–387 (1993), which is incorporated herein by reference).

A nucleic acid molecule, including a vector, can be introduced into a cell by any of a variety of methods known in the art (Sambrook et al., supra, 1989, and in Ausubel et al., Current Protocols in Molecular Biology, John Wiley and Sons, Baltimore, Md. (1994), which is incorporated herein by reference). Such methods include, for example, transfection, lipofection, microinjection, electroporation and infection with recombinant vectors or the use of liposomes.

Introduction of a nucleic acid molecule by infection with a viral vector is particularly advantageous in that it can efficiently introduce the nucleic acid molecule in to a cell ex vivo or in vivo. Moreover, viruses are very specialized and typically infect and propagate in specific cell types. Thus, their natural specificity can be used to target the nucleic acid molecule contained in the vector to specific cell types. For example, a vector based on a herpesvirus can be useful for targeting neuronal cells, whereas a vector based on HIV-1 can be useful for targeting T cells or macrophages. Viral or non-viral vectors also can be modified with specific receptors or ligands to alter target specificity through receptor mediated events.

A nucleic acid molecule encoding a Bax inhibitor protein, or an antisense molecule, also can be introduced into a cell using methods that do not require the initial introduction of the nucleic acid molecule into a vector. For example, the nucleic acid molecule can be introduced into a cell using a cationic liposomes, which also can be modified with specific receptors or ligands as described above (Morishita et al., J. Clin. Invest., 91:2580–2585 (1993), which is incorporated herein by reference). In addition, a nucleic acid molecule can be introduced into a cell using, for example, adenovirus-polylysine DNA complexes (see, for example, Michael et al., J. Biol. Chem., 268:6866–6869 (1993), which is incorporated herein by reference). Other methods of introducing a nucleic acid molecule into a cell such that an encoded Bax inhibitor protein or an antisense nucleic acid molecule can be expressed are well known (see, for example, Goeddel, supra, 1990).

Selectable marker genes encoding, for example, a polypeptide conferring neomycin resistance ($Neo^R$) also are readily available and, when linked to a nucleic acid molecule of the invention or incorporated into a vector containing the nucleic acid molecule, allows for the selection of cells that have incorporated the nucleic acid molecule. Other selectable markers such as those conferring hygromycin, puromycin or ZEOCIN (Invitrogen; San Diego Calif.) resistance are known to those in the art of gene transfer and can be used to identify cells containing an introduced nucleic acid molecule, including the selectable marker gene.

A "suicide" gene also can be incorporated into a vector so as to allow for selective inducible killing of a cell containing the gene. A gene such as the herpes simplex virus thymidine kinase gene (TK) can be used as a suicide gene to provide for inducible destruction of such cells. For example, where it is desired to terminate the expression of an introduced nucleic acid molecule encoding a Bax inhibitor protein, or an antisense molecule, in cells containing the nucleic acid molecule, the cells can be exposed to a drug such as acyclovir or gancyclovir, which can be administered to an individual.

Numerous methods are available for transferring nucleic acid molecules into cultured cells, including the methods described above. In addition, a useful method can be similar to that employed in previous human gene transfer studies, where tumor infiltrating lymphocytes (TILs) were modified by retroviral gene transduction and administered to cancer patients (Rosenberg et al., New Engl. J. Med. 323:570–578 (1990)). In that Phase I safety study of retroviral mediated gene transfer, TILs were genetically modified to express the neomycin resistance ($Neo^R$) gene. Following intravenous infusion, polymerase chain reaction analyses consistently found genetically modified cells in the circulation for as long as two months after administration. No infectious retroviruses were identified in these patients and no side effects due to gene transfer were noted in any patients. These retroviral vectors have been altered to prevent viral replication by the deletion of viral gag, pol and env genes. Such a method can also be used ex vivo to transduce cells taken from a subject (see Anderson et al., U.S. Pat. No. 5,399,346, issued Mar. 21, 1995, which is incorporated herein by reference).

When retroviruses are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. Hence, all retroviral vector supernatants used to infect cells are screened for replication competent virus by standard assays such as PCR and reverse transcriptase assays.

Where constitutive expression of a Bax inhibitor protein in cell is desired, the pBabe-PURO vector, which has been used for previous gene transfer studies of Bcl-2 and other genes into neuronal CMS14.1 and PC12 cells, can be particularly useful (Zhong et al., Proc. Natl. Acad. Sci., USA 90:4533–4537 (1993); Rabizadeh et al., Proc. Natl. Acad. Sci., USA 91:10703–10706 (1994), each of which is incorporated herein by reference). Where inducible expression of a Bax inhibitor protein is desired, the tetracycline-inducible vector pBSTR1, which encodes in a single vector a puromycin selectable marker and tetracycline repressor protein, can be particularly useful (Paulus et al., J. Virol. 60:62–67 (1996), which is incorporated herein by reference).

Moreover, pBSTR1 has a site for expression of a heterologous cDNA of interest from an internal CMV promoter that contains several tetracycline operators (Op) and that lies in reverse orientation relative to the LTRs, thereby avoiding "leakiness" in the expression of the desired cDNA in the absence of tetracycline through an antisense mechanism (Yu et al., *Cancer Res.* 56:5423–5427 (1996), which is incorporated herein by reference). This vector produces inducible clones at a ratio greater than 1:3. These retroviral constructs are packaged using the Phoenix cell system, which allows for transient production of high titers of recombinant viruses (Kitamura et al., *Proc. Natl. Acad. Sci., USA* 92:9146–9450 (1995); Ohishi et al., *Expt. Hematol.* 24:324–329 (1996), each of which is incorporated herein by reference).

The vesicular stomatitis virus glycoprotein (VSG) pseudotyping system also provides a vector system useful for introducing a nucleic acid molecule encoding a Bax inhibitor protein into a cell (Burns et al., *Proc. Natl. Acad. Sci., USA* 90:8033–8037 (1993), which is incorporated herein by reference). The packaging cells that produce VSG pseudotyped viruses can package the usual retroviral constructs, but substitute the VSG protein of the usual Moloney virus envelope proteins. VSG binds directly to phospholipids in biological membranes, rather than relying on the expression of a cell surface receptor protein and, therefore, can infect essentially all types of cells from all species and tissues.

The balance between cell production by mitogenesis and cell loss due to programmed cell death, which maintains the population of cells comprising a tissue or organ in a steady state, is disrupted in various pathological conditions. In some cancers, for example, increased expression of the anti-apoptotic Bcl-2 protein is associated with a decreased amount of programmed cell death of the tumor cells, resulting in the growth of a tumor. In comparison, elevated levels of the pro-apoptotic Bax protein occur in association with neurodegenerative diseases such as Parkinson's disease and Alzheimer's disease. Thus, dysregulation of Bcl-2 family proteins correlates with clinical features characteristic of various pathologies.

The Bcl-2 family of proteins regulate a distal step in the evolutionarily conserved pathway for programmed cell death and apoptosis, with the anti-apoptotic proteins such as Bcl-2 functioning as suppressors of cell death and the pro-apoptotic proteins functioning as promoters of cell death (Reed, *J. Cell Biol.* 124:1–6 (1994); Thompson, *Science* 267:1456–1462 (1995); Yang and Korsmeyer, *Blood* 88:386–401 (1996)). Since both anti-apoptotic proteins and pro-apoptotic proteins normally can be expressed in the same cell, the relative amount or activity of one of these classes of proteins as compared to the other class determines, in part, whether a cell is more or less likely to undergo apoptosis. In the simplest example, overexpression of an anti-apoptotic protein such as Bcl-2 in a cell generally results in a decreased likelihood that the cell will undergo apoptosis, whereas the overexpression of a pro-apoptotic protein such as Bax generally results in an increased likelihood that the cell will undergo apoptosis. However, the relationships of these proteins and their roles in regulating apoptotic activity will become apparent as the ability of such proteins to form homodimers or heterodimers and the effect of such homodimer or heterodimer formation is considered (see below).

Bcl-2 was the first identified member of a family of homologous proteins that regulate apoptosis. In particular, expression of Bcl-2 was associated with the failure of cells to undergo apoptosis and, therefore, Bcl-2 was identified as an anti-apoptotic protein. For example, overexpression of Bcl-2 blocks neuronal cell death that otherwise is induced in vitro by various stimuli, including neurotrophic factor withdrawal, calcium unifiers, various oxidants, glutamate, glucose deprivation, certain neurotrophic viruses, and amyloid β-peptide (Zhong et al., supra, 1993; Garcia et al., *Science* 258:302–304 (1992)). In addition, in vivo experiments involving Bcl-2 transgenic mice indicate that elevated levels of Bcl-2 can suppress neuronal cell death in the settings of focal ischemia and axotomy (Cenni et al., *Eur. J. Neurosci.* 8:1735–1745 (1996); Martinou et al., *Neuron* 13:1017–1030 (1994)). Under some circumstances, elevated levels of Bcl-2 also can inhibit necrotic cell death (Kane et al., *J. Neurosci. Res.* 40:269–275 (1995)).

In comparison to Bcl-2, Bax was the first identified member of the Bcl-2 family of proteins that have a pro-apoptotic action in cells. Elevations in Bax expression, due to gene transfer, promote cell death when triggered by a variety of initiators of apoptosis, including, for example, growth factor withdrawal, ionizing radiation, and anti-Fas antibody (Oltvai et al., *Cell* 74:609–619 (1993)). For example, Bax levels increase in hematopoietic, lymphoid and small intestine epithelial cells following irradiation (Kitada et al., *Oncogene* 12:187–192 (1996), which is incorporated herein by reference).

Conversely, mice rendered deficient in Bax expression, due to "knockout" of the bax gene, contain excessive numbers of cells in some tissues, including the brain, where the presence of increased numbers of sympathetic and facial motor neurons suggests a defect in developmental neuronal cell death (Deckwerth et al., *Neuron* 17:1401–411 (1996)). The absence of Bax expression in such knockout mice also prevents greater than 80% of the degeneration of facial motor neurons that normally occurs after axotomy. Embryonic neurons derived from Bax knockout mice are completely resistant to cell death induced by neurotrophic factor withdrawal, demonstrating an obligatory role for Bax in the death of sympathetic neurons when deprived of NGF (Id.). Similarly, ablation of Bax expression using antisense oligonucleotides protects sympathetic neurons from apoptosis induced by NGF withdrawal (Gillardon et al., *J. Neurosci. Res.* 43:726–734 (1996)).

Elevations in Bax expression occur in association with cell death induced by a variety of stimuli, including neuronal cell death that occurs due to ischemia, epilepsy, spinal cord injury, and certain neurodegenerative diseases such as Parkinson's disease and Alzheimer's disease. The Bax gene promoter contains p53 binding sites and is transcriptionally upregulated by p53 (Miyashita and Reed, *Cell* 80:293–299 (1995)). The elevation in p53 protein levels that occurs as an early event in various models of neuronal cell death induced by forebrain ischemia or by excitatoxic neurotransmitter administration suggests a role for Bax in such neuronal cell death (Manev et al., *J. Neurosci.* 16:1337–1345 (1994)).

Elevations in Bax levels occur as an early event associated with neuronal cell death due to brain ischemia (Krajewski et al., *J. Neurosci.* 15:6364–6376 (1995)) and Bax protein and mRNA levels rapidly increase in neurons within the penumbra region of focal infarcts in a model of middle cerebral artery occlusion in the rat (Gillardon et al., *Mol. Brain Res.* 40:254–260 (1996)). Elevations in Bax protein and mRNA levels also occur in neurons in vivo following excitatoxic lesion with the N-methyl-D-aspartate receptor agonist, quinolinic acid, or after systemic administration of kainic acid.

In addition to neuronal cell death associated with ischemia and excitatoxic neurotransmitters, Bax protein levels are markedly increased in sensory and motor neurons following sciatic nerve transection, often in association with increased in Jun protein production (Gillardon et al., *Brain Res.* 739:244–250 (1996)). The Bax gene promoter contains two consensus AP-1 sites. Elevations in Jun expression also occur in association with neuronal cell death induced by neurotrophic factor withdrawal, and microinjection of neutralizing anti-Jun antibodies can prevent such cell deaths (Estus et al., *J. Cell Biol.* 127:1717–1727 (1994)).

Increased Bax expression also occurs in spinal motor neurons in patients with amyotrophic lateral sclerosis (ALS; Mu et al., *Ann Neurol.* 40:379–386 (1996)). Amyloid β-peptide upregulates Bax and downregulates Bcl-2 expression in cultured human neurons, and systemic administration of 1-methyl-4-phenyl-1,2,3,6-tetrahydropyridine (MPTP) causes increases in Bax mRNA and protein in the substantia nigra (Hassouna et al., *Neurosci. Lett.* 204:85–88 (1996)). Marked elevations in Bax protein levels also occur in microglial cells and astrocytes in association with apoptosis in patients with HIV-induced encephalitis. These observations indicate that aberrant regulation of Bax expression contributes to pathology of neurodegenerative diseases.

Elevations in Bax expression also occur in residual myocardiocytes surrounding infarcts in the heart (Cheng et al., *Exp. Cell Res.* 226:316–327 (1996)), suggesting that increased Bax expression is a common occurrence during ischemia. The observation that stroke volumes are reduced by approximately half in Bax knockout mice treated by middle cerebral artery ligation provides further evidence of a cause and effect relation between increases in Bax expression and neuronal cell death induced due to ischemia.

In addition to a role for p53 induced expression of Bax in the induction of neuronal cell death, as discussed above, p53 induces an increase in Bax expression in some types of leukemia and solid tumor cells in response to genotoxic stress induced, for example, by chemotherapy or radiation therapy (Miyashita et al., *Oncogene* 9:1799–1805 (1994), which is incorporated herein by reference; Miyashita and Reed, supra, 1995). Furthermore, Bax gene mutations, which can inactivate one or both copies of the gene, are observed in various types of tumors (Rampino et al., *Science* 275:967–969 (1997), which is incorporated herein by reference). These observations indicate that proteins such as Bax inhibitor proteins, which modulate the Bax cell death pathway, can be used to improve the therapeutic responses of certain types of cancer.

Bcl-2 and Bax, as well as most other members of the Bcl-2 family of proteins, contain a stretch of hydrophobic amino acids near their C-termini that anchor the proteins in intracellular membranes. The Bcl-2 protein, for example, resides in the outer mitochondrial membrane, the nuclear envelope and the endoplasmic reticulum, whereas Bax localizes primarily to mitochondrial membranes. By immuno-electron microscopy, Bcl-2 appears to be concentrated at the junctional complexes in mitochondria and in nuclear pore complexes in the nuclear envelope, where the inner and outer membranes of these organelles contact. Since such sites are associated with ion and protein transport, the localization of Bcl-2 to such regions suggests it may be involved in ion or protein transport (dejong et al., *Cancer Res.* 54:256–260 (1994)).

The three dimensional structure of Bcl-$X_L$, which, like Bcl-2, is an anti-apoptotic member of the Bcl-2 family of proteins, indicates a close structural similarity to the pore-forming domains of certain bacterial toxins, including diphtheria toxin and the colicins A and E1. Moreover, measurements of ion efflux from unilammelar liposomes and from single channel recordings in planar lipid bilayers indicate that Bcl-2, Bcl-$X_L$ and Bax can form ion channels in membranes. However, the diameters of the channels formed by these Bcl-2 family proteins and the molecules, if any, that they transport in vivo have not been described. In this regard, diphtheria toxin transport its ADP-ribosylating subunit across biological membranes, whereas the colicins form nonspecific ion channels that kill bacteria by depolarizing them. Since Bcl-2 and Bax both can form membrane channels, they may transport proteins or ions in opposing directions, thereby accounting for the cytoprotective effects of Bcl-2 and the cytotoxic actions of Bax.

Overexpression of Bax in cells induces mitochondrial permeability transition pore (PTP) opening and activation of ICE/ced-3 family proteases (Caspases; see Xiang et al., *Proc. Natl. Acad. Sci., USA* 93:14559–14563 (1996)). Mitochondrial PTP, which is characterized by the dissipation of the electrochemical gradient, swelling of the matrix and eventual rupture of the outer mitochondrial membrane, represents a very early event associated with apoptosis and may be a central event where various upstream apoptosis initiating events converge into a final common pathway (Marchetti et al., *J. Exp. Med.* 184:1155–1160 (1996)).

In contrast to Bax, which induces mitochondrial PTP, Bcl-2 prevents mitochondrial PTP induction. At least three potentially lethal events occur following the induction of mitochondrial PTP: (1) reactive oxygen species, primarily superoxide anion, are generated due to interrupted electron chain transport; (2) $Ca^{2+}$ sequestered in the matrix is dumped into the cytosol; and (3) apoptogenic proteins that are stored in the intermembrane space and that activate Caspases are released (Liu et al., *Cell* 86:147–157 (1996)). Overexpression of Bcl-2 blocks all three of these events associated with apoptosis and mitochondrial PTP (Susin et al., *J. Exp. Med.* 184:1331–1342 (1996)), indicating that Bcl-2 may regulate mitochondrial PTP.

In cells in which the activation of Caspase was prevented by addition of peptidyl inhibitors of these cysteine proteases, overexpression of Bax induced mitochondrial PTP and production of superoxides and also induced cell death, but without generation of the usual proteolytic events and without the oligonucleosomal DNA fragmentation typical of apoptotic cell death. Under such conditions, Bax induced cytosolic vacuolarization and morphological changes more consistent with necrosis than apoptosis. Thus, by controlling mitochondrial PTP, Bcl-2 and Bax can modulate apoptosis and necrosis, with apoptosis involving the obligatory actions of the Caspases and necrosis emphasizing oxygen free radical production.

The Bcl-2 and Bax proteins can homodimerize and heterodimerize with each other, as well as with certain other members of the Bcl-2 protein family. A variety of mutagenesis studies indicate that some homodimerization and heterodimerization events are important for the function of Bcl-2 and Bax. For example, mutations in Bax that prevent homodimerization ablate the cytotoxic function of Bax in many, but not all, circumstances (Zha et al., *Mol. Cell Biol.* 16:6494–6508 (1996), which is incorporated herein by reference; Hunter and Parslow, *J. Biol. Chem.* 271:8521–8524 (1996); Simonian et al., *J. Biol. Chem.* 271:32073–32077 (1996)). Similarly, mutations in Bax that prevent its binding to Bcl-$X_L$ or Bcl-2 often, but not always, abrogate the pro-apoptotic effects of Bax in cells (Zha et al., supra, 1996); Simonian et al., *J. Biol. Chem.* 271:22764–22772 (1996)). Many, but not all, mutations in Bcl-2 or Bcl-$X_L$ that prevent binding to Bax also abrogate the anti-apoptotic effects of these proteins. Although the relevance to these various homodimerization and heterodimerization phenomenon to channel formation by Bcl-2 and Bax has not been described, the ability of Bcl-2 and Bax to create unique channels or negate each other by heterodimerizing may explain the observation that Bax can promote cell survival in some cellular contexts, apparently depending on the ratio of Bax to Bcl-2 (Middleton et al., *Development* 122:695–701 (1996)).

Bax induces cell death when expressed in either the budding yeast *S. cerevisiae* or the fission yeast *S. pombe*. As in mammalian cells, the lethal phenotype conferred by Bax in yeast can be suppressed by expression of anti-apoptotic Bcl-2 family proteins, including Bcl-2 and Bcl-$X_L$, but not by mutant versions of these proteins that fail to heterodimerize with Bax. Based on EM analysis, the cell death that occurs in Bax-expressing yeast resembles that in mammalian cells when treated with Caspase inhibitors, with massive cytosolic vacuolarization and only punctate chromatin condensation without the nuclear fragmentation and chromatin margination typical of apoptosis (Zha et al., supra, 1996). Consistent with this more necrotic morphology, there is no evidence of Caspase-like proteolytic activities in yeast. Mutagenesis experiments, in which the membrane anchoring domain of Bax was deleted or was swapped with mitochondria outer membrane-targeting domains from other proteins, indicated that the association with mitochondrial membranes is critical for Bax cytotoxic activity in yeast.

Based on these observations, a genetic screen was performed in yeast, which were genetically modified to express Bax, to identify suppressors of Bax mediated lethality. As disclosed herein, nucleic acid molecules encoding two Bax inhibitor proteins, BI-1 and BI-2, which suppress Bax-induced cytotoxicity in yeast, were identified. Accordingly, the present invention provides substantially purified Bax inhibitor proteins, including a BI-1 polypeptide having the amino acid sequence of SEQ ID NO: 3 (FIG. 1) and a BI-2 polypeptide having the amino acid sequence of SEQ ID NO: 6 (FIG. 2).

As used herein, the term "substantially purified," when used in reference to a Bax inhibitor protein (or polypeptide) of the invention, means that the protein is relatively free from contaminating lipids, proteins, nucleic acids or other cellular material normally associated with a Bax inhibitor protein in a cell. A substantially purified Bax inhibitor protein can be obtained, for example, by expressing a recombinant nucleic acid molecule such as SEQ ID NO: 1 or SEQ ID NO: 4 or can be substantially purified from a cell, for example, by affinity chromatography using a member of the Bcl-2 family of proteins such as Bax or Bcl-2 as a ligand or using an anti-Bax inhibitor protein antibody.

The amino acid sequences of BI-1 (SEQ ID NO: 3) and BI-2 (SEQ ID NO: 6) were deduced from their cDNA sequences (SEQ ID NO: 1 and SEQ ID NO: 4, respectively). BI-1 is a hydrophobic protein containing 237 amino acids and predicted to have six transmembrane domains (see Example I and FIG. 1). The molecular mass of BI-1 is calculated to be 26.4 kDa and an in vitro translation product of BI-1 migrates in SDS-PAGE at this mass. Expression in mammalian cells of BI-1 as a fusion protein with the green fluorescent protein (GFP) revealed a reticular cytosolic distribution typical of proteins associated with the endoplasmic reticulum (Example IV). Nuclear envelope fluorescence also was observed, as is typical for most ER-associated proteins.

BI-2 is a 450 amino acid RING finger protein predicted to contain two transmembrane domains (see Example I and FIG. 2). The RING finger domain of BI-2 comprises amino acids 34 to 73 and deletion of this domain produces a mutant BI-2 that does not suppress Bax induced cell death (Example II). The molecular mass of BI-2 is calculated to be 52.8 kDa and an in vitro translation product of BI-2 migrates in SDS-PAGE at this mass. Expression in mammalian cells of GFP-BI-2 fusion proteins also revealed localization in the endoplasmic reticulum and nuclear envelope, as was observed for BI-1. In addition, the GFP-BI-2 fusion protein localized in the mitochondria (Example IV). Thus, BI-1 and BI-2 colocalize intracellularly with members of the Bcl-2 family proteins, including Bcl-2 and Bax and, as disclosed herein, also can associate in vitro with Bcl-2 family proteins (Example V.A.).

The invention also provides peptide portions of Bax inhibitor proteins, comprising at least six contiguous amino acids of Bax inhibitor proteins shown as SEQ ID NO: 3 or SEQ ID NO: 6. Preferably, a peptide portion of a Bax inhibitor protein comprises at least ten contiguous amino acids of SEQ ID NO: 3 or SEQ ID NO: 6, more preferably at least twenty contiguous amino acids. A peptide portion of a Bax inhibitor protein can be useful, for example, for raising antibodies specific for a Bax inhibitor protein, such peptides being selected based, for example, on the criteria set forth below. In addition, a peptide portion of a Bax inhibitor protein such as a BI-2 deletion mutant lacking amino acid residues 34 to 73, corresponding to the RING domain, can be useful as a control in a drug screening assay of the invention (see below) or can be useful as a transdominant inhibitor of the wild type BI-2 protein. Furthermore, a peptide portion of BI-2 comprising the RING finger domain can be used to identify proteins that bind to BI-2 and are required for its Bax modulatory function. Such BI-2 binding proteins can be identified using well known methods for cloning interacting proteins, including, for example, the two hybrid assay or ligand blotting of a lambda phage cDNA expression library or affinity chromatography or the like.

The invention further provides antibodies specific for a Bax inhibitor protein such as BI-1 or BI-2. As used herein, the term "antibody" is used in its broadest sense to include polyclonal and monoclonal antibodies, as well as antigen binding fragments of such antibodies. With regard to an anti-Bax inhibitor protein iantibody of the invention, the term "antigen" means a Bax inhibitor protein, polypeptide or peptide portion thereof. An anti-Bax inhibitor protein antibody, or antigen binding fragment of such an antibody, is characterized by having specific binding activity for an epitope of a Bax inhibitor protein such as BI-1 or BI-2, or an peptide portion of a Bax inhibitor protein, of at least about $1\times10^5$ $M^{-1}$. Thus, Fab, F(ab')$_2$, Fd and Fv fragments of an anti-Bax inhibitor protein antibody, which retain specific binding activity for a Bax inhibitor protein, are included within the definition of an antibody.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference. These and other methods of making, for example, chimeric, humanized, CDR-grafted, single chain, and bifunctional antibodies are well known to those skilled in the art (Hoogenboom et al., U.S. Pat. No. 5,564,332, issued Oct. 15, 1996; Winter and Harris, *Immunol. Today* 14:243–246 (1993); Ward et al., *Nature* 341:544–546 (1989); Harlow and Lane, *Antibodies: A laboratory manual* (Cold Spring Harbor Laboratory Press, 1988); Hilyard et al., *Protein Engineering: A practical approach* (IRL Press 1992); Borrabeck, Antibody *Engineering*, 2d ed. (Oxford University Press 1995); each of which is incorporated herein by reference).

Anti-Bax inhibitor protein antibodies can be raised using as an immunogen a substantially purified Bax inhibitor protein such as BI-1 or BI-2, which can be prepared from natural sources or produced recombinantly, or a peptide portion of a Bax inhibitor protein as defined herein, including synthetic peptides as described above. A non-immunogenic peptide portion of a Bax inhibitor protein can be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art (see Harlow and Lane, supra, 1988; see, also, Hermanson, "Bioconjugate Techniques" (Academic Press 1996), which is incorporated herein by reference).

Particularly useful antibodies of the invention are those that bind to a Bax inhibitor protein that is in the form of a homodimer with a second Bax inhibitor protein (e.g., BI-1/BI-1 homodimers or BI-2/BI-2 homodimers) or that is in the form of a heterodimer with a Bcl-2 family protein, but not to the unbound (monomeric) Bax inhibitor protein. Similarly, antibodies that specifically bind to a Bax inhibitor protein homodimer, but not to a heterodimer, or to a heterodimer but not to a homodimer, also are useful. In addition, those antibodies that specifically bind to a monomeric Bax inhibitor protein, but not to the Bax inhibitor protein when it is in the form of a dimer are useful. Such antibodies of the invention can be used to identify the form of a Bax inhibitor protein in a cell and, therefore, can be useful for correlating particular forms of a Bax inhibitor protein to particular pathologies characterized by aberrant levels of apoptosis.

An anti-Bax inhibitor protein antibody also is useful for determining the presence or level of a Bax inhibitor protein in a tissue sample, which can be, for example, a lysate or a histological section. The identification of the presence or level of a Bax inhibitor protein in the sample can be made using well known immunoassay and immunohistochemical methods (Harlow and Lane, supra, 1988). An anti-Bax inhibitor protein antibody such as an anti-BI-1 antibody or an anti-BI-2 antibody also can be used to substantially purify BI-1 or BI-2, respectively, from a sample and, depending on the specificity of the antibody, as discussed above, can copurify an associated Bcl-2 family protein. In addition, an anti-Bax inhibitory protein antibody can be used in a screening assay to identify agents that alter the association of a Bax inhibitor protein and a second protein such as a second Bax inhibitor protein or a Bcl-2 family protein (see below).

A protein such as a Bax inhibitor protein or an anti-Bax inhibitor protein antibody can be labeled so as to be detectable using methods well known in the art (Hermanson, supra, 1996; Harlow and Lane, 1988; chap. 9). For example, a protein can be labeled with various detectable moieties including a radiolabel, an enzyme, biotin or a fluorochrome. Reagents for labeling a protein such as an anti-Bax inhibitor protein antibody can be included in a kit containing the antibody or can be purchased separately from a commercial source.

Following contact, for example, of a labeled antibody with a sample such as a tissue homogenate or a histological section of a tissue, specifically bound labeled antibody can be identified by detecting the particular moiety. Alternatively, a labeled second antibody can be used to identify specific binding of an unlabeled anti-Bax inhibitor protein antibody. A second antibody generally will be specific for the particular class of the first antibody. For example, if an anti-Bax inhibitor protein antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, which is an anti-Bax inhibitor protein antibody, then the sample is contacted with the labeled second antibody, which specifically binds to the anti-Bax inhibitor protein antibody and results in a labeled sample.

Methods for raising polyclonal antibodies, for example, in a rabbit, goat, mouse or other mammal, are well known in the art. In addition, monoclonal antibodies can be obtained using methods that are well known and routine in the art (Harlow and Lane, supra, 1988). Essentially, spleen cells from a Bax inhibitor protein-immunized mouse can be fused to an appropriate myeloma cell line such as SP/02 myeloma cells to produce hybridoma cells. Cloned hybridoma cell lines can be screened using a labeled Bax inhibitor protein to identify clones that secrete anti-Bax inhibitor protein monoclonal antibodies. Hybridomas expressing anti-Bax inhibitor protein monoclonal antibodies having a desirable specificity and affinity can be isolated and utilized as a continuous source of the antibodies, which are useful, for example, for preparing standardized kits containing the antibody. Similarly, a recombinant phage that expresses, for example, a single chain anti-Bax inhibitor protein also provides a monoclonal antibody that can used for preparing standardized kits.

Bcl-2 transgenic mice (line B6) can be particularly useful for obtaining monoclonal antibodies (Katsumata et al., *Proc. Natl. Acad. Sci., USA* 89:11376–11380 (1992), which is incorporated herein by reference). These transgenic mice produce human Bcl-2 protein at high levels in their B cells because of an immunoglobulin heavy chain enhancer present in the transgene. The enhanced survival of the B cells observed in these animals allows them to mount a superior secondary immune response, which can be exploited for increasing the frequency of antigen specific hybridomas. Using these animals, approximately 5-fold more positive hybridomas are obtained than when the traditional Balb/c mouse strain is used.

A monoclonal anti-Bax inhibitor protein antibody also can be used to prepare anti-idiotypic antibodies, which present an epitope that mimics the epitope recognized by the monoclonal antibody used to prepare the anti-idiotypic antibodies. Where the epitope to which the monoclonal antibody includes, for example, a portion of the Bax inhibitor protein involved in the ability of the protein to associate, for example, with a Bcl-2 family protein, the anti-idiotypic antibody can act as a competitor of Bax inhibitor protein binding and, therefore, can be useful for modulating apoptosis in a population of cells.

Peptide portions of BI-1 (DRKINFDALLKFSHITPSTQQHLKK; SEQ ID NO: 7) or BI-2 (DLERDEPLKSTGPQISVSE; SEQ ID NO: 8) were conjugated to KLH and OVA carrier proteins and used to immunize rabbits. Selection of a peptide portion of BI-1 or BI-2 for use as an immunogen was based on the following criteria, which, similarly, can be used to identify other peptide portions of BI-1 or BI-2 useful as immunogens. An immunogenic peptide, which can be inherently immunogenic or can be made immunogenic by conjugation to a carrier protein, generally is about 10 to about 30 amino acids in length, preferably about 20 amino acids; is hydrophilic and, therefore, likely to be exposed to solvent on a surface of the protein; has a mixture of acidic and basic amino acids; ideally contains at least 2 proline residues, preferably not more than 4 prolines, and the prolines are distributed at about ⅓ and ⅔ the distance along the peptide, preferably not at the N-terminus or C-terminus and preferably the prolines are not adjacent; ideally does not contain tryptophan, which is light sensitive, but can contain tryptophan if the sample is protected from light; contains a lysine or an arginine residue, preferably at least one of each; preferably does not contain methionine or histidine, which are subject to oxidative degradation; and can contain a cysteine, although, preferably, does not contain an internal cysteine, in which case a cysteine is added to the N-terminus or C-terminus, preferably the N-terminus, to facilitate conjugating the peptide to a maleimide-activated carrier protein. The selected peptide portion then is compared against the Swiss Protein database to confirm that the peptide does not share fortuitous homology with a known protein, the presence of a stretch of six or more perfect matches being grounds for discarding the peptide. Where a peptide portion has solubility problems, the solution is made to 10% dimethyl sulfoxide (DMS) and, if required, can be increased up to 50% DMSO without preventing conjugation to the maleimide-activated carrier protein.

In addition, recombinant GST-fusion proteins, comprising soluble peptide portions of BI-2, specifically the N-terminal region where the RING domain is located (amino acids 1 to 139; SEQ ID NO: 4) and the loop located between the two predicted transmembrane domains (amino acids 167 to 358; SEQ ID NO: 4) have been prepared and these GST-fusion proteins have been affinity purified and used to immunize. These GST-BI-2 fusion proteins also can be used to immunize the Bcl-2 transgenic mice (line B6) to generate mouse monoclonal antibodies.

The invention also provides methods of using a BI-1 or BI-2 polypeptide, or a peptide portion thereof, and nucleic acid molecules encoding these polypeptides, to identify the presence of a second protein such as another Bax inhibitor protein or Bcl-2 family protein in a sample. Such a method is based on the present disclosure that a Bax inhibitor protein can form homodimers and, in addition, can specifically associate with a member of the Bcl-2 family of proteins such as Bcl-2 or Bax to form a heterodimer (see Example III.A.).

As used herein, the term "associate" or "association," when used in reference to a Bax inhibitor protein and a second protein means that the Bax inhibitor protein and the second protein have a binding affinity for each other such that they form a bound complex in vivo or in vitro, including in a cell in culture or in a reaction comprising substantially purified reagents. For convenience, the term "bind" or "interact" is used interchangeably with the term "associate."

The affinity of binding of a Bax inhibitor protein and a second protein such as Bax is characterized in that it is sufficiently specific such that a bound complex can form in vivo in a cell or can form in vitro under appropriate conditions as disclosed herein (see Example III.A.). The formation or dissociation of a bound complex can be identified, for example, using a two hybrid assay or demonstrating coimmunoprecipitation of the second protein with the Bax inhibitor protein using antibodies of the invention as disclosed herein. Methods for distinguishing the specific association of an Bax inhibitor protein and a second protein from nonspecific binding are known in the art and, generally, include performing the appropriate control experiments to demonstrate the absence of nonspecific protein binding. For example, an appropriate control can include showing that the second protein binds to the Bax inhibitor protein, but not to a mutant Bax inhibitor protein such as to a mutant BI-2 lacking the RING finger domain.

As used herein, the term "second protein" refers to a protein that specifically associates with a Bax inhibitor protein. Such a second protein is exemplified herein by Bax and Bcl-2, which are involved in cell death pathways leading to apoptosis of a cell. A second protein also can be a protein that is upstream or downstream of a Bax inhibitor protein in cell death pathway and associates with the Bax inhibitor protein, or can be a second protein that associates with the Bax inhibitor protein in a cell, thereby regulating the ability of the Bax inhibitor protein to associate, for example, with a Bcl-2 family protein. Agents that alter the association of a Bax inhibitor protein and a second protein can be extremely valuable, for example, for modulating the level of apoptosis in a population of cells. A Bax inhibitor protein such as BI-1 or BI-2 can be used in a drug screening assay of the invention because, prior to the present disclosure, BI-1 and BI-2 were not known to have the ability to associate with other proteins such as Bcl-2 family proteins.

A second protein can be a regulatory protein that associates with a Bax inhibitor protein. Such a regulatory protein can inhibit a Bax inhibitor protein binding ability depending, for example, on whether the regulatory protein is associated with the Bax inhibitor protein. While not wishing to be bound to a particular mechanism as to how a regulatory protein can affect the activity of a Bax inhibitor protein, the association of a regulatory protein with a Bax inhibitor protein can, for example, block (or reveal) a membrane targeting domain such as a mitochondrial membrane targeting domain of a Bax inhibitor protein, thereby modulating the likelihood that the Bax inhibitor protein can interact with a Bcl-2 family protein. The ability of a regulatory protein to associate with, or dissociate from, a Bax inhibitor protein can depend, for example, on the relative phosphorylation state of the regulatory protein.

The invention further provides methods of identifying agents that can modulate the formation of Bax inhibitor protein homodimers or that modulate the binding of a Bax inhibitor protein to a member of the Bcl-2 family of proteins. Such a method is useful, for example, for screening large libraries of molecules to identify those agents that can alter homodimer or heterodimer formation and, therefore, are most likely to be useful as drugs for treating pathologies characterized by aberrant levels of apoptosis.

As used herein, the term "modulate" or "alter" when used in reference to the association of a Bax inhibitor protein and a second protein, means that the affinity of the association is increased or decreased. Agents that can alter the association of a Bax inhibitor protein with a second protein can be useful for modulating apoptosis in a population of cells and, therefore, can be useful as medicaments for treating a pathology characterized by an aberrant level of apoptosis. Such an agent can be, for example, an anti-idiotypic antibody as described above, which can inhibit the association of a Bax inhibitor protein and a second protein.

A screening assay of the invention is particularly useful to identify, from among a diverse population of molecules, those agents that modulate the association of a Bax inhibitor protein and a second protein. Methods for producing libraries containing diverse populations of molecules, including chemical or biological molecules such as simple or complex organic molecules, peptides, proteins, peptidomimetics, glycoproteins, lipoproteins, polynucleotides, and the like, are well known in the art (Huse, U.S. Pat. No. 5,264,563, issued Nov. 23, 1993; Blondelle et al., Trends Anal. Chem. 14:83–92 (1995); York et al., Science 274:1520–1522 (1996); Gold et al., Proc. Natl. Acad. Sci., USA 94:59–64 (1997); Gold, U.S. Pat. No. 5,270,163, issued Dec. 14, 1993). Such libraries also can be obtained from commercial sources.

Since libraries of diverse molecules can contain as many as $10$ to $10^{15}$ different molecules, a screening assay of the invention provides a simple means for identifying those agents in the library that can modulate the association of a Bax inhibitor protein and a second protein. In particular, a screening assay of the invention can be automated, which allows for high through-put screening of randomly designed libraries of agents to identify those particular agents that can modulate the ability of a Bax inhibitor protein and a second protein to associate.

A drug screening assay of the invention utilizes a Bax inhibitor protein such as BI-1 or BI-2, which can be expressed, for example, from a nucleic acid molecule encoding the amino acid sequence shown in SEQ ID NO: 3 or SEQ ID NO: 6, respectively, or can be purified from a sample containing the Bax inhibitory protein by affinity chromatography, for example, utilizing a GST-Bax fusion protein or a histidine$_6$ (His-6)-Bax fusion protein as the ligand. For example, when a Bax inhibitor protein is used in a screening assay, the solid substrate can contain a covalently attached glutathione molecule, which can bind a GST-Bax inhibitor protein fusion protein, or a covalently bound anti-Bax inhibitor protein antibody, provided that the antibody binds the Bax inhibitor protein without interfering with its ability to associate with the second protein. If desired, the Bax inhibitor protein can be expressed as a GST- or His-6-fusion protein, which can facilitate binding to a solid substrate for use in an in vitro drug screening assay (see Example V.B.).

A drug screening assay to identify an agent that alters the association of a Bax inhibitor protein and a second protein can be performed by allowing, for example, the Bax inhibitor protein, or Bax inhibitor protein-fusion protein to bind to the solid support, then adding the second protein, which can be a Bcl-2 family member such as Bax, Bcl-2, Bak, Bad or the like, and an agent to be tested, under conditions suitable for the association of the Bax inhibitor protein and second protein in the absence of a drug (see Example V). If desired, the Bax inhibitor protein or the second protein is detectably labeled so as to facilitate identification of the association. Control reactions, which contain or lack either, the Bax inhibitor protein (or fusion protein), or the second protein, or the agent, or which substitute the Bax inhibitor protein with a mutant Bax inhibitor protein such as BI-2 lacking the RING finger domain, which lacks the ability to suppress Bax-induced cell death, also are performed. Following incubation of the reaction mixture, the amount of the second protein that is specifically bound to the Bax inhibitor protein in the presence of an agent can be determined and compared to the amount of binding in the absence of the agent so that agents that modulate the association can be identified.

A transcription activation assay such as the two hybrid assay, which can be performed in yeast cells or mammalian cells, allows the identification of protein-protein interactions and, further, can be particularly useful as the basis for a drug screening assay (Fields and Song, Nature 340:245–246 (1989); Fearon et al., Proc. Natl. Acad. Sci., USA 89:7958–7962 (1992), each of which is incorporated herein by reference). Such an assay provides the advantage that the drug screening assay is performed in cells in culture and, therefore, as compared to an in vitro drug screening assay, identifies agents that alter the association of a Bax inhibitor protein and a second protein under more physiological conditions in a living cell. Such agents can be identified by detecting an altered level of transcription of a reporter gene, the expression of which is dependent on the association of a Bax inhibitor protein and a second protein, as compared to the level of transcription in the absence of the agent.

Where the drug screening assay using the two hybrid system is performed in yeast, an agent may not be able to cross the yeast cell wall and, therefore, cannot enter the yeast cell to alter a protein-protein interaction. The use of yeast spheroplasts, which are yeast cells that lack a cell wall, can circumvent this problem (Smith and Corcoran, In Current Protocols in Molecular Biology (ed. Ausubel et al.; Green Publ., N.Y. 1989), which is incorporated herein by reference). In addition, an agent, upon entering a cell, may require "activation" by a cellular mechanism that may not be present in yeast. Activation of an agent can include, for example, metabolic processing of the agent or a modification such as phosphorylation of the agent, which can be necessary to confer activity upon the agent. In this case, a mammalian cell line can be used to screen a panel of agents (Fearon et al., supra, 1992).

An agent that alters the association of a Bax inhibitor protein and a second protein such as a Bcl-2 family protein can be useful as a drug to reduce the severity of a pathology characterized by aberrant apoptotic activity. Various pathologies are characterized by an increased or decreased level of apoptosis as compared to the normal level of apoptosis for a particular population of cells. For example, decreased levels of apoptosis occur in cancer cells, resulting in the ability of a tumor to form amidst otherwise normal cells in a tissue or organ. In addition, increased levels of apoptosis are associated with a number of neurological disorders including stroke, epilepsy, spinal cord injury, head trauma, and certain neurodegenerative diseases. Thus, by manipulating the expression of a Bax inhibitor protein in cells involved in such pathologies or by altering the interactions of Bax inhibitor proteins as they occur in such cells, improvements can be effected to treatment of the disease.

As discussed above, Bax levels are increased in regions of focal cerebral infarcts, as occurs in an individual suffering a stroke. Similarly, Bax levels are increased upon exposure of cells to radiation, such as occurs during radiation therapy for cancer. Associated with these increases in Bax expression are increased levels of apoptosis. Thus, methods for modulating Bax activity, for example, in neuronal cells following a stroke or in normal tissue cells present within the irradiation field of a tumor can be useful for minimizing the amount of undesirable cell death that otherwise occurs in such situations. As disclosed herein, Bax activity can be modulated by contacting the appropriate cell population with an agent, for example, that modulates the action of a Bax inhibitor protein such as BI-1 or BI-2 such that the Bax inhibitor protein can suppress Bax induced cell death. Such agents, therefore, are useful as medicaments for treating a pathology characterized, in part, by aberrantly increased amounts of Bax induced cell death. Alternatively, expression of an antisense Bax inhibitor protein nucleic acid molecule such as the antisense molecules shown as SEQ ID NO: 2 and SEQ ID NO: 5, in cells in which it is desired to suppress Bax induced cell death, can suppress such cell death.

The skilled artisan will recognize the broader usefulness of such agents and antisense molecules for therapeutic treatment of many of the pathologic conditions discussed above, each of which is characterized, in part, by aberrant levels of programmed cell death. Furthermore, the artisan would recognize that such methods can be used for altering the level of apoptosis in cells, where such levels are determined by the expression of various combinations of Bcl-2 family proteins, including combinations of pro-apoptotic and anti-apoptotic proteins. In particular, the role of Bax inhibitor proteins in modulating the activity of Bcl-2 family proteins such as Bad, Bak, and the like can be determined using methods as disclosed herein and, where the aberrant activity of such Bcl-2 family proteins is involved in a pathologic condition and where the activity of such proteins is modulated by a Bax inhibitor protein, a method of the invention can be used to ameliorate the severity of such conditions.

The following examples are intended to illustrate but not limit the present invention.

EXAMPLE I IDENTIFICATION AND CHARACTERIZATION OF BI-1 AND BI-2 cDNA and AMINO ACID SEQUENCES This example describes methods for isolating and characterizing BI-1 and BI-2 cDNA and amino acid sequences.

A. Cloning of BI-1 and BI-2

Nucleic acid molecules encoding BI-1 and BI-2 were identified by suppression of Bax-induced death of yeast cells transformed to express human Bax. *S. cerevisiae* yeast strain QX95001 was constructed by transforming the plasmid YEp51-Bax, which encodes and expresses human Bax, into yeast strain BF264-15Dau (MATα ade1 his2 leu2-3,112 trp1-1a ura3 (Lew et al., *Cell* 66:1197–1206 (1991), which is incorporated herein by reference). YEp51-Bax (Zha et al., supra, 1996) is a URA3-marked yeast high copy plasmid containing a full length mouse Bax cDNA under the control of the galactose-inducible yeast GAL10 promoter. QX95001 cells were verified to express Bax and to die upon being shifted from glucose to galactose-containing medium.

A human HepG2 cDNA library, under the control of the yeast GAP1 promoter and, therefore, expressible in yeast cells, was used for library screening. QX95001 cells were grown to mid-log phase (approximately $2 \times 10^7$ cells/ml) in standard YPD liquid medium (Schiestl and Giest, *Curr. Genet.* 16:339–346 (1989), which is incorporated herein by reference) and approximately 100 μg of the HepG2 cDNA library plasmids DNA were introduced by a lithium acetate transformation procedure.

Bax resistant transformants were directly selected on galactose-containing solid medium. An aliquot of the transformation mixture also was streaked on glucose-containing medium to determine transformation efficiency. Seventy-five Bax resistant colonies were obtained from a screen of approximately $1 \times 10^6$ transformants (assayed five days after transformation). These yeast colonies were patched onto galactose medium as a secondary screen to confirm their ability to overcome Bax-induced cytotoxicity. Seventeen colonies were Bax-resistant in the secondary screen.

Bax-resistant colonies can result either from the presence of a human cDNA in the transformed yeast cells or from a yeast gene mutation that suppresses Bax function in these cells. To distinguish between these possibilities, a "concomitant loss" ("Con loss") assay was applied. If the Bax-resistance phenotype was caused by expression of a gene product from a cDNA in the HepG2 library, then the loss of the library plasmid, as indicated by the concomitant loss of the plasmid marker, URA3, would result in loss of the Bax-resistance phenotype. In contrast, if Bax-resistance was caused by an endogenous yeast gene mutation, then the loss of the library plasmid should not have any impact on the Bax-resistance phenotype.

The "Con-loss" assay was performed on the 17 positive clones isolated from the secondary screening, above, and four clones (clones 6, 8, 25, and 32) exhibited the expected phenotype. The Con-loss assay was performed as described by Ausubel et al. (supra, 1991). Although not further examined, the ability of remaining thirteen clones to survive Bax killing likely is due to mutations in the yeast strain.

Plasmid DNA was recovered from the 4 "Con-loss" positive clones and reintroduced into strain QX95001, which contains the galactose-inducible YEpSl-Bax plasmid to confirm that these plasmids suppress Bax-induced yeast cell death. Nucleotide sequence analysis of the cDNA inserts in the plasmids revealed that three contained overlapping nucleotide sequences, all of which had a complete ORF encoding a 237 amino acid protein (BI-1; SEQ ID NO: 3), whereas the fourth clone contained a unique nucleotide sequence, including an ORF encoding a 450 amino acid protein (BI-2; SEQ ID NO: 6).

B. Bax Inhibitor Protein-1 (BI-1)

cDNA inserts of the Bax inhibitor clones 6, 8, 25 and 32 were liberated from the yeast vector by cutting with Bgl II and subcloned into the Bam HI site of pUC18. DNA sequencing was accomplished by the dividing nucleotide chain termination method using SEQUENASE and, as primers, 5'-CAGCACTGACCCTTTTG-3' (SEQ ID NO: 15) and 5'-AGCGGATAACAATTTCACACAGGA-3' (SEQ ID NO: 16), according to the manufacturer's instructions (Perkin Elmer Co.; Foster City Calif.); additional internal primers corresponding to different portions of the BI-1 (or BI-2, below) cDNA were constructed as required based on the sequencing data.

The inserts of clones 6, 25 and 32 represented overlapping fragments of the same 2634 bp cDNA (SEQ ID NO: 1 and SEQ ID NO: 2), which contained an open reading frame encoding a predicted 237 amino acid protein (SEQ ID NO: 3; FIG. 1). Based on functional studies as disclosed herein, the encoded protein was designated Bax inhibitor protein-1 (BI-1).

The BI-1 nucleotide sequence was used to search nucleotide sequence databases using the BLAST program (Altschul et al., *J. Mol. Biol.* 215:403–410 (1990)). The cDNA encoding BI-1 was very similar to a previously cloned cDNA named TEGT (Walter et al., supra, 1995), although the TGET cDNA contained no in-frame stop codon upstream of the predicted open reading frame (ORF), whereas the disclosed cDNA encoding BI-1 contains an additional 33 bp at the 5'-end, as compared to TEGT, including an in-frame stop codon beginning 57 bp upstream of the initiator methionine, ATG, codon (see SEQ ID NO: 1; upstream stop codon, TAG, at positions 16–18; initiator methionine ATG at positions 73–75; ORF extends from 73–783).

The amino acid sequence of BI-1 was deduced from the clone 6, 25, and 32 cDNA sequences (FIG. 1; SEQ ID NO: 3). A Kyte-Doolittle plot revealed that BI-1 has six potential transmembrane domains (underlined in FIG. 2; Kyte and Doolittle, *J. Mol. Biol.* 157:105–132 (1982)). The N-terminus and C-terminus of BI-1 contain hydrophilic stretches of amino acids.

C. Bax Inhibitor Protein-2 (BI-2)

The sequence of the clone 8 cDNA insert also was examined. The insert was liberated from the yeast plasmid by digestion with Bgl II, subcloned into the BamHI site of pUC18 and sequenced as described above for BI-1. The cDNA contained 2531 bp, including an in-frame stop codon located at position −6 bp and an ORF (see SEQ ID NO: 4; upstream stop codon, TAA, at positions 148–150; initiator methionine, ATG, at positions 154–156; ORF extends from 154–1503).

The ORF encodes a predicted protein, designated "BI-2," having 450 amino acids (SEQ ID NO: 6; FIG. 2), including a RING domain (FIG. 2; bold print) and two predicted transmembrane domains (FIG. 2, underlined). A database search revealed that BI-2 shares homology only with some short unidentified fragments in the EST database (Accession Numbers gb:N30481; gb:AA181642; gb:N28421; gb:R88757; gb:T35285; gb:AA071433; gb:AA021128; emb:Z45856/HSCZVG111; gb:R91016; emb:Z45333/HSC2MH031; emb:F07927/HSC2MH041; gb:R12025; gb:T09074; emb:Z44193/HSC1UE031; gb:R67734; gb:T35906; gb:AA233437; gb:R01296; gb:R00170; emb:F04224/HSC2MH042; gb:AA181590; gb:R58120; gb:AA171676; gb:N35575; emb:F05632/HSC0HC121; gb:AA096046; gb:W36836; emb:F04223/HSC2MH032; and gb:R01185).

D. In vitro-Translation of the BI-1 and BI-2 Proteins

The BI-1 and BI-2 cDNAs were cloned into the Bam HI site of plasmid pcDNA3 (Invitrogen, Inc.; La Jolla Calif.) and in vitro transcription was accomplished using the T7 promoter present in pcDNA3. For BI-1, the ORF was excised from pUC18 (see Example I.B.) using Xba I and Stu I, the ends were blunted with Klenow polymerase, and cDNA was ligated into Eco RV-linearized pcDNA3, generating plasmid pcDNA3-BI-1. For BI-2, the ORF was excised from pUC18 (see Example I.C.) using Eco RI and Xba I and cloned between the Eco RI and Xba I sites of pcDNA3, generating pcDNA3-BI-2.

In vitro transcription/translation was performed using the TNT method, according to the manufacturer's instructions (Promega Corp.; Madison Wis.). The reaction mixture, containing 1 μg plasmid DNA, 12.5 μl of TNT rabbit reticulocyte lysate, 1 μl TNT buffer, 0.5 μl of amino acids mix, minus methionine, 0.5 μl RNAsin (20 units), 0.5 μl T7 RNA polymerase, and 20 μCi $^{35}$S-labeled methionine (1000 μCi/mmol), was incubated at 30° C. For in vitro translation of BI-1, 0.1% TRITON was included in the reaction to help maintain solubility of the protein.

The resulting proteins were analyzed by SDS-PAGE and autoradiography. The radiolabeled protein bands were consistent with the predicted molecular masses of BI-1 (26.4 kDa) and BI-2 (52.8 kDa). HA-tagged versions of these proteins also were prepared from the mammalian expression plasmid pcDNA3. Expression of the tagged proteins resulted in the expected size for BI-1 and BI-2 having three copies of HA tag appended to their N-termini.

EXAMPLE II

BI-1 AND BI-2 SUPPRESS BAX-INDUCED APOPTOSIS IN YEAST

This example demonstrates that BI-1 and BI-2 can suppress the ability of Bax to induce cell death in yeast genetically modified to express a mammalian Bax protein.

Plasmids were recovered from the four "Con-loss" positive clones (Example I.A.) and transformed into the parental yeast strain, QX95001, which expresses Bax under the control of the GAL10 promoter. Transformants containing the BI-1 plasmid (pQX36−1) or the BI-2 plasmid (pQX36-2), as well QX95001 cells transformed with clone 6 (BI-1) or clone 8 (BI-2), and untransformed QX95001 cells were streaked onto solid medium containing galactose and incubated at 30° C. for four days.

Very little growth of the parental strain, QX95001 was observed on galactose medium. In contrast, the BI-1 (pQX36-1) and BI-2 (pQX36-2) transformants and the original cDNA library transformants, clone 6 (BI-1) and clone 8 (BI-2), produced substantial growth when grown on the same medium. These results demonstrate that the expression of BI-1 or BI-2 in yeast cells that express Bax allows the cells to grow under conditions that otherwise are not permissive for growth.

In order to exclude the possibility that BI-1 and BI-2 reduce Bax protein levels in yeast, for example, by affecting transcription from the yeast GAL10 promoter, 1 μg of pQX36-1 (BI-1) or pQX36-2 (BI-2) was cotransformed into yeast cells with 1 μg of pEG202-bax under the control of the strong ADH1 promoter (Sato et al., *Proc. Natl. Acad. Sci., USA* 91:9238–9242 (1994); Sato et al., *Gene* 140:291–292 (1994), each of which is incorporated herein by reference). Transformants were streaked on synthetic drop-out medium lacking uracil and histidine and allowed to grow for 4 days at 30° C. to select for cells containing plasmids expressing Bax, BI-1 and BI-2. Significant growth was observed only in transformants containing the pQX36-1 (BI-1) or the pQX36-2 (BI-2) plasmid. These results confirm that the expression of BI-1 or BI-2 prevented Bax-induced killing, regardless of the promoter from which Bax is expressed.

The possibility that BI-1 or BI-2 expression in yeast suppressed Bax protein expression also was examined. QX95001 strain yeast were transformed with the YEp51-Bax plasmid, alone (control), or with pQX36-1 (BI-1) or with pQX26-2 (BI-2). Yeast were grown in glucose medium, then an aliquot was transferred to galactose medium and grown for an additional 20 hr. Lysates were prepared from each culture, protein extracts were normalized for total protein content and 25 μg protein was subjected to SDS-PAGE and western blot using an anti-mouse Bax antiserum for detection (Krajewski et al., *Amer. J. Pathol.* 145:1323–1333 (1994), which is incorporated herein by reference).

Similar levels of Bax protein were detected in the galactose-induced cells, regardless of whether the BI-1 and BI-2 plasmids were coexpressed. These results demonstrate that the inhibitory effect on cell death due to expression of BI-1 or BI-2 was not due to inhibition of Bax expression in the cells.

EXAMPLE III

BI-1 AND BI-2 MODULATE BAX-INDUCED APOPTOSIS IN MAMMALIAN CELLS

This example demonstrates that BI-1 and BI-2 can modulate the cell death pathway that involves Bax in mammalian cells.

A. Human 293 Kidney Cells:

The ability of BI-1 and BI-2 to abrogate Bax-induced cell death in 293 human embryonic kidney cells also was examined (Zha et al., supra, 1996), which is incorporated herein by reference). 293 cells were plated at about $5\times10^5$ cells per 60 mm dish and transfected using calcium phosphate precipitation with the following plasmids: (1) 9 μg pcDNA3 ("vector control"); (2) 3 μg pcDNA3-Bax (Zha et al., supra, 1996) and 6 μg pcDNA3; (3) 3 μg pcDNA3-Bax and 6 μg pcDNA-BI-1; (4) 3 μg pcDNA3-Bax and 6 μg pcI-BI-2; (5) 3 μg pcDNA3-Bax and 6 μg pcDNA3-BI-2ΔR, which encodes a BI-2 deletion mutant lacking amino acid residues 34 to 73, corresponding to the RING domain; see FIG. 2, SEQ ID NO: 6; (6) 3 μg pcDNA3-Bax and 6 μg PCR/CMV-Bcl-2; or (7) 6 μg pcDNA-3 and 3 μg pCMV-β-galactosidase. After 24 hours, adherent cells were recovered by trypsinization and pooled with floating (dead) cells. The percentage of dead cells was determined by trypan blue exclusion. Three independent experiments were performed. To determine the transfection efficiency, the cells transfected with pCMV-β-gal were fixed in 2% paraformaldehyde and 0.1% glutaraldehyde and incubated with 30 μg/ml X-gal in PBS for 18 hr, revealing approximately 80% blue cells.

Bax cotransfected with the negative control pcDNA3 parental plasmid caused cell death in approximately 25% of the cells, based on trypan blue dye exclusion. In contrast, only about 3% of cells transfected with the pcDNA3 "empty" vector were dead. Cotransfection of the BI-1 or BI-2 expression plasmids with Bax reduced cell death by 2.5 to 5-fold, with only about 5% to 10% of the cells failing to exclude trypan blue dye. The extent to which BI-1 and BI-2 abrogated Bax-induced cell death was similar to that observed when a Bcl-2 encoding plasmid was cotransfected with Bax. Expression of the BI-2 mutant lacking the RING domain failed to suppress Bax-induced cell death.

B. Ability of Bax Inhibitor Protein to Promote Apoptosis

Since Bax can promote IL-3 withdrawal-induced apoptosis in the pro-B lymphocyte cell line FL5.12 (Oltvai et al., supra, 1993), the ability of BI-1 and BI-2 to affect IL-3 withdrawal-induced death of FL5.12 cells was examined. FL5.12 cells were transfected with pcDNA3-BI-1-HA, pcDNA3-HA-BI-2 or pcDNA3-Bax by electroporation using a GENEPULSER set at 250 V and 1050 mF (Biorad; Hercules Calif.).

The plasmid pcDNA3-BI-1-HA, which expresses BI-1 linked at its C-terminus to the HA tag, was prepared in two steps. The C-terminus of BI-1, from the internal Bam HI site, was PCR amplified to add an Xho I site to the C-terminal end of the BI-1 ORF. PCR primers used were 5'-GGGGATCCATTTGGCCTTTCCAG-3' (SEQ ID NO: 9) and 5'-GGCTCGAGTTTTCTTCTCTTTCTTCTTATCC-3 (SEQ ID NO: 10). The PCR product was cleaved with Bam HI and Xho I and cloned into the C-terminal HA tagged version of the pcDNA3, to produce plasmid pQX9645. The N-terminal portion of BI-1, encoded by a 0.5 kbp Bam HI fragment obtained from pcDNA3-BI-1, was inserted into pQX9645, giving rise to full length BI-1 polypeptide containing the HA tag at the its C-terminus.

Two days after transfection of the FL5.12 pro-B cells, GENETICIN (G418) was added to a final concentration of 1 mg/ml and the cells were maintained in medium containing G418. Stably transfected, G418-resistant cells were obtained after about 2 weeks of selection. Pools of stably transfected FL5.12 cells were subcloned by limited dilution and individual clones were subjected to IL-3 withdrawal-induced apoptosis assay as previously described (Oltvai et al., supra, 1993). Briefly, cells were seeded at $2\times10^5$ cells/ml. After 24 hr, the cells were washed three times with serum-free, IL-3-free medium, then seeded, in triplicate, in IL-3-free, serum-containing medium at $5\times10^5$ cells/ml. At various time intervals, samples were taken and examined by trypan blue staining.

Expression of BI-1 or BI-2, with or without an HA tag, in FL5.12 cells did not protect the cells from IL-3 withdrawal-induced apoptosis, but, instead, accelerated cell death. Survival of cells expressing BI-1 or BI-2 was essentially the same as the survival of FL5.12 cells expressing Bax. These results suggest that BI-1 and BI-2 may be able to modulate, either positively or negatively, cell survival, depending on the cellular context. This finding is consistent with the observation that BI-2 can heterodimerize with both anti-apoptotic proteins, like. Bcl-2, and pro-apoptotic proteins, like Bax. Thus, the ability of BI-1 and BI-2 to have a pro-appptotic or anti-apoptotic effect may depend on the relative ratio of Bcl-2 and Bax inside the particular cell type.

EXAMPLE IV

EXPRESSION OF BI-1 AND BI-2 IN CELLS AND TISSUES

This example demonstrates that BI-1 and BI-2 are intracellular proteins that are ubiquitously expressed in various tissues.

A. Intracellular Localization of BI-1 and BI-2

The subcellular localization of BI-1 and BI-2 was determined by expressing these proteins as fusion proteins with the green fluorescent protein (GFP). BI-1 or BI-2 was fused with a double mutant (F64L; S65T) of GFP using the vectors pEGFP-N2 and pEGFP-C2 (Clontech Laboratories, Inc.; Palo Alto Calif.). BI-2 was subcloned from the pSN503-BI-2 plasmid (see below) into pEGFP-C2 using the Eco RI and Sal I sites, resulting in expression of BI-2 fused in-frame with the upstream GFP sequences. BI-1 was subcloned inframe from either pSN503-BI-1 (see below) or pcDNA3-HA-BI-1 plasmid into either pEGFP-C2 or pEGFP-N2, resulting in expression of BI-1 fused to either the N-terminus or C-terminus of GFP.

The plasmid pSN503-BI-1, which expresses BI-1 tagged at its N-terminus to HA, was prepared by PCR amplifying the BI-1 CDNA to add an Eco RI site to the sequence encoding the N-terminal end of BI-1 (in-frame with the HA tag) and to add an Xho I site to sequence encoding the C-terminal end of BI-1. The resulting PCR product was cleaved with Eco RI and Xho I and ligated into Eco RI and Xho I cleaved pSN503, which is based on pcDNA3 and contains three copies of the HA tag (Wang et al., *Proc. Natl. Acad. Sci., USA* 93:7063–7068(1996), which is incorporated herein by reference). PCR primers used were 5'-GGGAATTCAACATATTTGATCGAAAGATC-3' (SEQ ID NO: 11) and 5'-GGCTCGAGTCATTTCTTCTCTTTCTTCTT-3' (SEQ ID NO: 12).

The plasmid pSN503-BI-2, which expresses BI-2 tagged at its N-terminus to HA, also was cloned into the HA-tagged pSN503 vector by PCR. The N-terminus of BI-2 (up to the internal Hpa I site) was PCR amplified to add an Eco RI site to the very N-terminus of the BI-2 ORF (in-frame with the pSN503 HA tag). PCR primers used were 5'-GGGAATTCATGGAGGAACCTCAGAAAAGC-3' (SEQ ID NO: 13) and 5'-GAAGATGCCCACCATAAAGCA-3' (SEQ ID NO: 14). This PCR amplified BI-2 N-terminus was used to replace a similar EcoRI-HpaI fragment of pcDNA3-BI-2 (see above), to produce plasmid pQX96421. The EcoRI-XbaI BI-2 containing fragment was cloned into pSN503 at the EcoRI-XbaI site, generating plasmid pSN503-BI-2.

The GFP-BI-1 fusion proteins were expressed by transient transfection into 293 cells, GM701 cells or Cos-7 cells. After 2 days, fluorescence confocal microscopy was performed. In all three cell lines, GFP-BI-1 fusion proteins (both N-terminal fusions and C-terminal fusions) exhibited a reticular cytosolic distribution typical of proteins associated with the endoplasmic reticulum (ER). Nuclear envelope fluorescence also was observed, as is typical for most ER-associated proteins. The GFP-BI-2 fusion protein exhibited the same ER/nuclear envelope distribution. However, the BI-2 fusion protein also was associated with cytosolic organelles.

In order to determine the cytosolic organelles that BI-2 was associated with, medium was removed and cells were incubated with 20 nM MITOTRACKER (Molecular Probes, Inc.; Eugene Oreg.) in fresh medium for 20 min. Cells then were washed with PBS and fixed in 3.7% paraformaldehyde for 15 min at room temperature. After fixation, cells were washed twice with PBS and mounted in VECTASHIELD Mounting medium (Vector Laboratories, Inc.; Burlingame Calif.). Fluorescence confocal microcopy was performed using an AXIOPHOT photomicroscope (Zeiss Inc., Oberkochen, Germany). Based on colocalization with the rhodamine-like, mitochondria-specific fluorochrome, MITOTRACKER (Molecular Probes, Inc.), it was determined that BI-2 localizes in the mitochondria.

These results indicate that BI-2 displays an intracellular localization very similar to the localization of Bcl-2 and Bcl-$X_L$, whereas BI-1 was distributed in a pattern more similar to the Bcl-2 homologs Mcl-1 and Bak, as well as the Alzheimer's disease-associated proteins presenilin-1 and presenilin-2.

B. Expression of BI-1 and BI-2 in Tissues

A BI-1 cDNA fragment was excised from pSN503-BI-1 using Eco RI and Xho I and a BI-2 cDNA fragment was excised from pSN503-BI-2 using Eco RI and Hind III. The cDNA fragments were labeled with $\alpha$-$^{32}$P-dCTP (3000 Ci/mmol; DuPont) using the RADPRIME DNA Labeling kit (GIBCO/BRL; Gaithersburg Md.). Briefly, the 50 $\mu$l reaction mixture contained 50 ng BI-1 (or BI-2) cDNA, 1 $\mu$l each of dATP, dGTP and dTTP, 20 $\mu$l of 2.5 x random primers solution (provided with kit), 5 $\mu$l $\alpha$-$^{32}$P-dCTP (50 $\mu$Ci), 1 $\mu$l Klenow (40 units) and double distilled water. The labeling reaction was carried out at 37° C. for 15 min, and terminated by adding 5 $\mu$l Stop Buffer, which was provided with the kit. Probes were purified by spinning through SEPHADEX minicolumns to remove unincorporated $\alpha$-$^{32}$P-dCTP.

The labeled BI-1 or BI-2 CDNA was used to probe a HUMAN MULTIPLE TISSUE NORTHERN BLOT (Clontech) using the EXPRESSION HYBRIDIZATION protocol (Clontech). The northern blot was prehybridized in the EXPRESSHYB solution at 62° C. for 1 hr in a shaking water bath. Labeled probe was denatured by heating at 95° C. for 5 min, then mixed with fresh EXPRESSHYB solution (2×10$^6$ cpm/ml) and added to the northern blot. Hybridization was carried out at 62° C. for 2 hr, then the blot was washed 2×20 min in wash solution 1 (2×SSC {0.3 M NaCl and 0.03 M sodium citrate}, 0.05% SDS) at room temperature, followed by 2×20 min in wash solution 2 (0.1×SSC, 0.1% SDS) at 50° C., then was subjected to autoradiography.

Both BI-1 and BI-2 were expressed in most tissues, including brain. Notably, two different size transcripts were detected for both BI-1 and BI-2, with major mRNAs of 2.9 kbp and 1.0 kbp for BI-1 and of 3.0 kbp and 1.5 kbp for BI-2. Moreover, only the 2.9 kbp BI-1 transcript and the 3.0 kbp BI-2 transcript were detectable in brain. It remains to be determined whether these different size transcripts arise from alternative splicing mechanisms and whether they encode different proteins.

EXAMPLE V

USE OF BI-1 AND BI-2 IN A DRUG SCREENING ASSAY

This example demonstrates that BI-2 specifically associates with either Bax or Bcl-2 to form heterodimers or with itself to form homodimers and describes an assay for screening for agents such as drugs that alter the association of BI-1 or BI-2 and a member of the Bcl-2 family of proteins.

A. Binding of BI-2 to Bcl-2 Family Proteins

*E. coli* containing the various GST constructs were grown to an O.D. 600 of about 0.8. IPTG was added to a final concentration of 0.5 mM and induction was carried out at 30° C. for 4 hr. Bacterial cells were lysed by sonication in lysis buffer (50 mM Hepes, 2 mM EDTA, 150 mM NaCl, 5 mM $\beta$-mercaptoethanol, 1 mM PMSF, 1% NP-40 and 1 mg/ml lysozyme). The lysates were incubated with glutathione SEPHAROSE beads at 4° C. for 2 hr, then the beads were washed 4× with binding buffer (142.5 mM KCl, 5 mM MgCl$_2$, 10 mM Hepes (pH 7.2), 1 mM EGTA, 0.20% NP-40, 0.5 mM DTT).

GST fusion proteins were prepared as follows. BI-2 was cloned into the GST fusion vector pGEX-4T1 (Pharmacia Biotech Inc., Piscataway N.J.) by cleaving pSN503-BI-2 with Xba I and blunting the ends with Klenow polymerase. The fragment then was digested with Eco RI to release the BI-2 fragment. The pGEX-4T1 vector was cleaved with Xho I, blunt-ended with Klenow polymerase, then cleaved again with Eco RI. The BI-2 fragment and linearized vector were ligated, to produce pGEX-4T1-BI-2, which expresses the GST-BI-2 fusion protein. GST-CD40 (Sato et al., supra, 1995) and GST-BAX (Hanada et al., *J. Biol. Chem.* 270:11962–11968 (1995), which is incorporated herein by reference) were produced as previously described.

Approximately 5 $\mu$g of the following fusion proteins, including GST control, GST-CD40 cytosolic domain, GST-Bcl-2, GST-Bax or GST-BI-2, were immobilized on glutathione SEPHAROSE, then 8 $\mu$l of $^{35}$S-labeled in vitro translated HA-tagged BI-2 in binding buffer was added. After incubation at 4° C. for 2 hr, the beads were washed 5× with binding buffer and the associated proteins were eluted in Laemli sample buffer and analyzed by SDS-PAGE (10% gel). As a control, $^{35}$S-labeled BI-2 was loaded directly into the gel, using one-quarter the amount employed for the binding experiments. Following electrophoresis, the gels were dried and exposed to X-ray film.

In vitro translated HA-tagged BI-2 bound to GST-Bax, GST-Bcl-2, and GST-BI-2, but not to GST or to GST-CD40. These results demonstrate that BI-2 can form heterodimers in vitro with the Bcl-2 family proteins Bcl-2 and with Bax, but not with an unrelated protein (CD40). In addition, the results demonstrate that BI-2 can form homodimers or homo-oligomers in vitro.

B. In Vitro Drug Screening Assay

A GST-BI-1 or GST-BI-2 fusion protein or His-6-fusion protein can be prepared using methods as described above or otherwise known in the art and purified using glutathione- or metal-chelation chromatography, respectively (Smith and Johnson, *Gene* 67:31–40 (1988), which is incorporated herein by reference). The fusion protein then is immobilized to a solid support taking advantage of the ability of the GST protein to specifically bind glutathione or of the His-6 peptide region to chelate a metal ion such as nickel (Ni) ion or cobalt (Co) ion (Clontech) by immobilized metal affinity chromatography. Alternatively, an anti-BI-1 antibody or anti-BI-2 antibody can be immobilized on a matrix and BI-1 or BI-2, respectively, can be allowed to bind to the antibody. If desired, the proteins also can be allowed to adsorb to plastic wells, as is routine for ELISA procedures.

The Bcl-2 family protein, which can be Bcl-2, Bax, Bad, Bak, Bcl-$X_S$ or BCl-$X_L$, for example, can be detectably labeled with a moiety such as a fluorescent molecule or a radiolabel (Hermanson, supra, 1996), then contacted in solution with the immobilized BI-1 or BI-2 under conditions as described in Example V.A., which allow a Bax inhibitor protein to specifically associate with a Bcl-2 family protein. Preferably, the reactions are performed in 96 well plates, which allows for automated reading of the reactions. Alternatively, the Bcl-2 family protein such as Bax or Bcl-2 can be detected by a colorimetric ELISA method using specific antibodies. In addition, BI-2 can be added with an epitope tag, such as HA or FLAG for an ELISA based drug assay. Various agents such as drugs then are screened for the ability to alter the association of the Bax inhibitor protein and the Bcl-2 family protein.

The agent and labeled Bcl-2 family protein can be added together to the immobilized BI-1 or BI-2, incubated to allow binding, then washed to remove unbound labeled Bcl-2 family protein. The relative amount of binding of labeled Bcl-2 family protein in the absence as compared to the presence of the agent being screened is determined by detecting the amount of label remaining in the plate. Appropriate controls are performed to account, for example, for nonspecific binding of the labeled Bcl-2 family protein to the matrix. Such a method allows the identification of an agent that alter the association of a Bax inhibitor protein such as BI-1 or BI-2 and a Bcl-2 family protein such as Bcl-2 or Bax.

Alternatively, the labeled Bcl-2 family protein can be added to the immobilized Bax inhibitor protein and allowed to associate, then the agent can be added. Such a method allows the identification of agents that can induce the dissociation of a bound complex comprising the Bax inhibitor protein and the Bcl-2 family protein.

C. Cell Based Screening Assay

A cell based drug screening assay also can be established using, for example, yeast or mammalian cells transfected with BI-1 or BI-2. For example, 293 cells can be transfected with expression plasmids producing Bax and BI-1 or BI-2, such that survival of the Bax expressing cells is dependent on BI-1 or BI-2 expression. The cells then can be used in 96 well plate format for screening libraries of agents, in order to identify agents that suppress the effect of BI-1 or BI-2, thereby allowing Bax induced cell death to occur. The viability of 293 cells can be monitored using routine assays such as the MTT dye reduction assay or histone/DNA ELISA (Boehringer-Mannheim Corp.; Indianapolis Ind.). As a control for agents that nonspecifically kill the 293 cells, untransfected 293 cells are examined in parallel.

Similarly, yeast cells can be used in a drug screening assay of the invention. Yeast cells that are genetically modified to express Bax and either BI-1 or BI-2 are used to screen for agents that can suppress BI-1 or BI-2 function, thus allowing Bax expression to kill the cells. As a control for nonspecific killing, untransfected yeast cells, which do not express Bax, are evaluated in parallel. The viability or growth of yeast cells can be monitored by optical absorbance at 500–600 nm or by other methods such as selective protein staining, which can identify viable cells.

Although the invention has been described with reference to the examples provided above, it should be understood that various modifications can be made without departing from the spirit of the invention. Accordingly, the invention is limited only by the claims.

We claim:

1. An isolated cell line producing an antibody, or antigen-binding fragment thereof, that specifically binds to a Bax inhibitor protein selected from the group consisting of SEQ ID NO: 3 and SEQ ID NO: 6.

2. The cell line of claim 1, which is a hybridoma cell line.

3. An isolated antibody, or antigen-binding fragment thereof, which specifically binds to a Bax inhibitor protein selected from the group consisting of SEQ ID NO: 3 and SEQ ID NO: 6.

4. The isolated antibody or antigen-binding fragment of claim 3, which specifically binds to SEQ ID NO: 3.

5. The isolated antibody or antigen-binding fragment of claim 3, which specifically binds to SEQ ID NO: 6.

6. The isolated antibody or antigen-binding fragment of claims 3, 4 or 5, which is polyclonal.

7. The isolated antibody or antigen-binding fragment of claim 3, 4 or 5, which is monoclonal.

8. The isolata anyibody or antigen-binding fragment of claim 3, 4 or 5, which is an antigen-binding fragment selected from the group consisting of a Fab, F(ab')2, Fd and Fv fragment.

9. An isolated cell line producing an antibody, or antigen-binding fragment thereof, that specifically binds to SEQ ID NO: 3.

10. An isolated cell line producing an antibody, or antigen-binding fragment thereof, that specifically binds to SEQ ID NO: 6.

* * * * *

UNITED STATES PATENT AND TRADEMARK OFFICE
CERTIFICATE OF CORRECTION

PATENT NO. : 6,545,128 B1
DATED : April 8, 2003
INVENTOR(S) : Reed et al.

It is certified that error appears in the above-identified patent and that said Letters Patent is hereby corrected as shown below:

Column 48,
Line 20, please delete "isolata anyibody", replace therefor with -- isolated antibody --.

Signed and Sealed this

Thirteenth Day of July, 2004

JON W. DUDAS
*Acting Director of the United States Patent and Trademark Office*

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 2634 base pairs
      (B) TYPE: nucleic acid
      (C) STRANDEDNESS: single
      (D) TOPOLOGY: linear (xi) SEQUENCE DESCRIPTION: SEQ ID NO: 1:

```
TGTTAGAAGC GCTGGTAGGC CTTGGAGAGG CGGGTTAGGA AGAGTGGAGA CTGCTGCACG      60

GACTCTGGAA CCATGAACAT ATTTGATCGA AAGATCAACT TTGATGCGCT TTTAAAATTT     120

TCTCATATAA CCCCGTCAAC GCAGCAGCAC CTGAAGAAGG TCTATGCAAG TTTTGCCCTT     180

TGTATGTTTG TGGCGGCTGC AGGGGCCTAT GTCCATATGG TCACTCATTT CATTCAGGCT     240

GGCCTGCTGT CTGCCTTGGG CTCCCTGATA TTGATGATTT GGCTGATGGC AACACCTCAT     300

AGCCATGAAA CTGAACAGAA AAAACTGGGA CTTCTTGCTG GATTTGCATT CCTTACAGGA     360

ATTGGCCTGG GCCCTGCCCT GGAGTTTTGT ATTGCTGTCA ACCCCAGCAT CCTTCCCACT     420

GCTTTCATGG GCACGGCAAT GATCTTTACC TGCTTCACCC TCAGTGCACT CTATGCCAGG     480

CGCCGTAGCT ACCTCTTTCT GGGAGGTATC TTGATGTCAG CCCTGAGCTT GTTGCTTTTG     540

TCTTCCCTGG GGAATGTTTT CTTTGGATCC ATTTGGCTTT TCCAGGCAAA CCTGTATGTG     600

GGACTGGTGG TCATGTGTGG CTTCGTCCTT TTTGATACTC AACTCATTAT TGAAAAGGCC     660
```

```
GAACATGGAG ATCAAGATTA TATCTGGCAC TGCATTGATC TCTTCTTAGA TTTCATTACT      720

GTCTTCAGAA AACTCATGAT GATCCTGGCC ATGAATGAAA AGGATAAGAA GAAAGAGAAG      780

AAATGAAGTG ACCATCCAGC CTTTCCCAAT TAGACTTCCT CTCCTTCCAC CCCTCATTTC      840

CTTTTTGCAC ACATTACAGG TGGTGTGTTC TGTGATAATG AAAAGCATCA GAAAAGCTTT      900

TGTACTTTGT GGTTTCCTCT ATTTTGAATT TTTTGATCAA AAAACTGATT AGCAGAATAT      960

AGTTTGGAGT TTGGCTTCAT CTTCCTGGGG TTCCCCTCAC TCCCTTTTTT GTCAACCCCA     1020

TCTGTAGCCT CTTCCTCTAC TCAGGCAGTC GACCCGCCAC GATGAGAAGT GGGACCAGCC     1080

AGAGGGCGCC AACTTCAGGA GTCCGCTTTC CCACCAGGCT TCATTCACCC AGTGGACCTG     1140

AACTGTTTGG TAGAGCCACC CGGCCCTTCC TTCCTCATTG TTGTTTGGTA TGCGCACAGT     1200

TCCTGTGGGA CTGGGCCGTG AGTTTTCCAT GGAAAGAAA TTCAGTGGTC CCATTGTTAA     1260

CTCAACCTCA AATCTCAACT GTCAGGCCCT ACAAAGAAAA TGGAGAGCCT CTTCTGGTGG     1320

ATGCTTTGCT CCCTCTGAGC TGCCCATGCT GGTCTGGCAA ACACACCTTT CTGCTTTGCC     1380

TTCACAAAAG TAATGTGTTC CCTTTCCCAC CCCTTGCCTG ACCCTCAGGG AGTCAGCCTG     1440

CTTCCATCCA TGGGTGGGAA GACTTCAGCA CAAAGGAAAG ACTAATTCTT GTCAGGCATT     1500

TTTGAAAAGG CTGATTATGT GTATCAAGGT ACAGCTACGT AGGTTCCCCT AAACTTGCCC     1560

TGTTTTTGTT TTTTTAGTTT GTTATCCCCT TACTGAGCGG CCTCTACTAG GTGGCTGTGA     1620

TTAAATGTCC CAAGCAAGGA TAGGGAAGGG GAATGGTTGA GCCTCTGGAG ATCATTGTAA     1680

CCAATCCTGC CAGACCTGTT TGGGGCAGTG GGGAGCAAAC CTAGATAAGG ACCTGTTTGG     1740

GGCAGCAGGG AGCAAAATCT CCTTTAACAA CCAAGCAGTT CCTCATTCAC ATCAACAGAG     1800

CGAGGCTGTG ATAACTTAGG AGGCAGCAAT CCTAATAGTC CTTCAGTGCA TTTTAGTCTG     1860

TCTCCAACTG GACACCAGTA GGTAGTGTCA AGCCAGAGAT TCGGGGCAGT AGATAAATGT     1920

TCATTTTACT GATGCACTTT AGTTTTTGGT CTGTTACCTG TTTTCCAGAA ATTTGTGGCC     1980

TTTTAGGCGG GAGTTAGGCG ACCAAACCAG TGAGAGCCCC AATCCCTGCA GTTTTGTGGC     2040

TTCAAGTGTG GGTGGACAGT CCTAATGGGG ATCTCCAGCT CCTTCCTGTG GGCTGCCACA     2100

GACAGCTACC CCCAAAAGGG TCAATGTTGG GAGTGGTTGT GGCTCTGAAC TGCTCTACAG     2160

AGCTTCAGTG TGAGAGGATC GAGCCATTGA AAGCTCATTA CCAGTAGGAC ATAATTTTTG     2220

GCTCTCCCTA TTCACAACCA GTGCACAGTT TGACACAGTG GCCTCAGGTT CACAGTGCAC     2280

CATGTCACTG TGCTATCCTA CGAAATCATT TGTTTCTAAG TTGTGTTTAT TCCTGGAGTG     2340

ACATGCCACC CCGAATGGCT CACTTTCACT GAGGATGCTG TCCTCTGATT TAGCTGCTGC     2400

CTCCAGCCTC TGGCTTGAGA ACTTACTAAA GGCACTTCCT TCCTGTTAAA CCCCTGTTAA     2460

CTCTCCATAA ATTTGGTGAT TCTCTGCTAG GCCTAAGATT TTGAGTTAAC ATCTCTTGAA     2520

GCCAAACTCC ACCTTCTGTG CTTTTTGCTT GGGATAATGG AGTTTTTCTT TAGAAACAGT     2580

GCCAAGAATG ACAAGATATT AAAAAAAAAA AAAAAAAAA AAAAAAAAA AAAA           2634
```

(2) INFORMATION FOR SEQ ID NO: 2:

(i) SEQUENCE CHARACTERISTICS:
        (A) LENGTH: 2634 base pairs
        (B) TYPE: nucleic acid
        (C) STRANDEDNESS: single
        (D) TOPOLOGY: linear (xi) SEQUENCE DESCRIPTION: SEQ ID NO: 2:

```
TTTTTTTTTT TTTTTTTTTT TTTTTTTTTT TTTTAATATC TTGTCATTCT TGGCACTGTT       60
```

```
TCTAAAGAAA AACTCCATTA TCCCAAGCAA AAAGCACAGA AGGTGGAGTT TGGCTTCAAG      120

AGATGTTAAC TCAAAATCTT AGGCCTAGCA GAGAATCACC AAATTTATGG AGAGTTAACA      180

GGGGTTTAAC AGGAAGGAAG TGCCTTTAGT AAGTTCTCAA GCCAGAGGCT GGAGGCAGCA      240

GCTAAATCAG AGGACAGCAT CCTCAGTGAA AGTGAGCCAT TCGGGGTGGC ATGTCACTCC      300

AGGAATAAAC ACAACTTAGA AACAAATGAT TTCGTAGGAT AGCACAGTGA CATGGTGCAC      360

TGTGAACCTG AGGCCACTGT GTCAAACTGT GCACTGGTTG TGAATAGGGA GAGCCAAAAA      420

TTATGTCCTA CTGGTAATGA GCTTTCAATG GCTCGATCCT CTCACACTGA AGCTCTGTAG      480

AGCAGTTCAG AGCCACAACC ACTCCCAACA TTGACCCTTT TGGGGGTAGC TGTCTGTGGC      540

AGCCCACAGG AAGGAGCTGG AGATCCCCAT TAGGACTGTC CACCCACACT TGAAGCCACA      600

AAACTGCAGG GATTGGGGCT CTCACTGGTT TGGTCGCCTA ACTCCCGCCT AAAAGGCCAC      660

AAATTTCTGG AAAACAGGTA ACAGACCAAA AACTAAAGTG CATCAGTAAA ATGAACATTT      720

ATCTACTGCC CCGAATCTCT GGCTTGACAC TACCTACTGG TGTCCAGTTG GAGACAGACT      780

AAAATGCACT GAAGGACTAT TAGGATTGCT GCCTCCTAAG TTATCACAGC CTCGCTCTGT      840

TGATGTGAAT GAGGAACTGC TTGGTTGTTA AAGGAGATTT GCTCCCTGC TGCCCCAAAC       900

AGGTCCTTAT CTAGGTTTGC TCCCCACTGC CCCAAACAGG TCTGGCAGGA TTGGTTACAA      960

TGATCTCCAG AGGCTCAACC ATTCCCCTTC CCTATCCTTG CTTGGGACAT TTAATCACAG     1020

CCACCTAGTA GAGGCCGCTC AGTAAGGGGA TAACAAACTA AAAAAACAAA AACAGGGCAA     1080

GTTTAGGGGA ACCTACGTAG CTGTACCTTG ATACACATAA TCAGCCTTTT CAAAAATGCC     1140

TGACAAGAAT TAGTCTTTCC TTTGTGCTGA AGTCTTCCCA CCCATGGATG GAAGCAGGCT     1200

GACTCCCTGA GGGTCAGGCA AGGGGTGGGA AAGGGAACAC ATTACTTTTG TGAAGGCAAA     1260

GCAGAAAGGT GTGTTTGCCA GACCAGCATG GGCAGCTCAG AGGGAGCAAA GCATCCACCA     1320

GAAGAGGCTC TCCATTTTCT TTGTAGGGCC TGACAGTTGA GATTTGAGGT TGAGTTAACA     1380

ATGGGACCAC TGAATTTCTT TCCAATGGAA AACTCACGGC CCAGTCCCAC AGGAACTGTG     1440

CGCATACCAA ACAACAATGA GGAAGGAAGG GCCGGGTGGC TCTACCAAAC AGTTCAGGTC     1500

CACTGGGTGA ATGAAGCCTG GTGGGAAAGC GGACTCCTGA AGTTGGCGCC CTCTGGCTGG     1560

TCCCACTTCT CATCGTGGCG GGTCGACTGC CTGAGTAGAG GAAGAGGCTA CAGATGGGGT     1620

TGACAAAAAA GGGAGTGAGG GGAACCCCAG GAAGATGAAG CCAAACTCCA AACTATATTC     1680

TGCTAATCAG TTTTTTGATC AAAAAATTCA AAATAGAGGA AACCACAAAG TACAAAAGCT     1740

TTTCTGATGC TTTTCATTAT CACAGAACAC ACCACCTGTA ATGTGTGCAA AAAGGAAATG     1800

AGGGGTGGAA GGAGAGGAAG TCTAATTGGG AAAGGCTGGA TGGTCACTTC ATTTCTTCTC     1860

TTTCTTCTTA TCCTTTTCAT TCATGGCCAG GATCATCATG AGTTTTCTGA AGACAGTAAT     1920

GAAATCTAAG AAGAGATCAA TGCAGTGCCA GATATAATCT TGATCTCCAT GTTCGGCCTT     1980

TTCAATAATG AGTTGAGTAT CAAAAAGGAC GAAGCCACAC ATGACCACCA GTCCCACATA     2040

CAGGTTTGCC TGGAAAAGCC AAATGGATCC AAAGAAAACA TTCCCAGGG AAGACAAAAG      2100

CAACAAGCTC AGGGCTGACA TCAAGATACC TCCCAGAAAG AGGTAGCTAC GGCGCCTGGC     2160

ATAGAGTGCA CTGAGGGTGA AGCAGGTAAA GATCATTGCC GTGCCCATGA AAGCAGTGGG     2220

AAGGATGCTG GGGTTGACAG CAATACAAAA CTCCAGGGCA GGGCCCAGGC CAATTCCTGT     2280

AAGGAATGCA AATCCAGCAA GAAGTCCCAG TTTTTTCTGT TCAGTTTCAT GGCTATGAGG     2340

TGTTGCCATC AGCCAAATCA TCAATATCAG GGAGCCCAAG GCAGACAGCA GGCCAGCCTG     2400
```

```
AATGAAATGA GTGACCATAT GGACATAGGC CCCTGCAGCC GCCACAAACA TACAAAGGGC    2460

AAAACTTGCA TAGACCTTCT TCAGGTGCTG CTGCGTTGAC GGGGTTATAT GAGAAAATTT    2520

TAAAAGCGCA TCAAAGTTGA TCTTTCGATC AAATATGTTC ATGGTTCCAG AGTCCGTGCA    2580

GCAGTCTCCA CTCTTCCTAA CCCGCCTCTC CAAGGCCTAC CAGCGCTTCT AACA          2634
```

(2) INFORMATION FOR SEQ ID NO: 3:

(i) SEQUENCE CHARACTERISTICS:
        (A) LENGTH: 237 amino acids
        (B) TYPE: amino acid
        (D) TOPOLOGY: linear (xi) SEQUENCE DESCRIPTION: SEQ ID NO: 3:

```
Met Asn Ile Phe Asp Arg Lys Ile Asn Phe Asp Ala Leu Leu Lys Phe
1               5                   10                  15

Ser His Ile Thr Pro Ser Thr Gln Gln His Leu Lys Lys Val Tyr Ala
                20                  25                  30

Ser Phe Ala Leu Cys Met Phe Val Ala Ala Gly Ala Tyr Val His
            35                  40                  45

Met Val Thr His Phe Ile Gln Ala Gly Leu Leu Ser Ala Leu Gly Ser
        50                  55                  60

Leu Ile Leu Met Ile Trp Leu Met Ala Thr Pro His Ser His Glu Thr
65                  70                  75                  80

Glu Gln Lys Lys Leu Gly Leu Leu Ala Gly Phe Ala Phe Leu Thr Gly
                85                  90                  95

Ile Gly Leu Gly Pro Ala Leu Glu Phe Cys Ile Ala Val Asn Pro Ser
                100                 105                 110

Ile Leu Pro Thr Ala Phe Met Gly Thr Ala Met Ile Phe Thr Cys Phe
            115                 120                 125

Thr Leu Ser Ala Leu Tyr Ala Arg Arg Arg Ser Tyr Leu Phe Leu Gly
        130                 135                 140

Gly Ile Leu Met Ser Ala Leu Ser Leu Leu Leu Ser Ser Leu Gly
145                 150                 155                 160

Asn Val Phe Phe Gly Ser Ile Trp Leu Phe Gln Ala Asn Leu Tyr Val
                165                 170                 175

Gly Leu Val Val Met Cys Gly Phe Val Leu Phe Asp Thr Gln Leu Ile
            180                 185                 190

Ile Glu Lys Ala Glu His Gly Asp Gln Asp Tyr Ile Trp His Cys Ile
        195                 200                 205

Asp Leu Phe Leu Asp Phe Ile Thr Val Phe Arg Lys Leu Met Met Ile
        210                 215                 220

Leu Ala Met Asn Glu Lys Asp Lys Lys Glu Lys Lys
225                 230                 235
```

(2) INFORMATION FOR SEQ ID NO: 4:

(i) SEQUENCE CHARACTERISTICS:
        (A) LENGTH: 2531 base pairs
        (B) TYPE: nucleic acid
        (C) STRANDEDNESS: single
        (D) TOPOLOGY: linear (xi) SEQUENCE DESCRIPTION: SEQ ID NO: 4:

```
CGAAGCCTCT CCCTCTTCCT CTGCTCCCGC GGGGTCTGTG CTGAGAATAA TGGCCCGGTT      60

GGCCCGGGAC GAGTGGAATG ATTAATGATG TTTTGCAGCA GTTTTCTACG TCTGAAATTT     120

TTTATGTCTC TGGAACCCAG AATTTGCTAA GAGATGGAGG AACCTCAGAA AAGCTATGTG     180
```

-continued

```
AACACAATGG ACCTTGAGAG AGATGAACCT CTCAAAAGCA CCGGCCCTCA GATTTCTGTT      240
AGTGAATTTT CTTGCCACTG CTGCTACGAC ATCCTGGTTA ACCCCACCAC CTTGAACTGT      300
GGGCACAGCT TCTGCCGTCA CTGCCTTGCT TTATGGTGGG CATCTTCAAA GAAAACAGAA      360
TGTCCAGAAT GCAGAGAAAA ATGGGAAGGT TTCCCCAAAG TCAGTATTCT CCTCAGGGAT      420
GCCATTGAAA AGTTATTTCC TGATGCCATT AGACTGAGAT TTGAAGACAT TCAGCAGAAT      480
AATGACATAG TCCAAAGTCT TGCAGCCTTT CAGAAATATG GAATGATCA GATTCCTTTA       540
GCTCCTAACA CAGGCCGAGC GAATCAGCAG ATGGGAGGGG GATTCTTTTC CGGTGTGCTC      600
ACAGCTTTAA CTGGAGTGGC AGTGGTCCTG CTCGTCTATC ACTGGAGCAG CAGGGAATCT      660
GAACACGACC TCCTGGTCCA CAAGGCTGTG GCCAAATGGA CGGCGGAAGA AGTTGTCCTC      720
TGGCTGGAGC AGCTGGGCCC TTGGGCATCT CTTTACAGGG AAAGGTTTTT ATCTGAACGA      780
GTAAATGGAA GGTTGCTTTT AACTTTGACA GAGGAAGAAT TTTCCAAGAC GCCCTATACC      840
ATAGAAAACA GCAGCCACAG GAGAGCCATC CTCATGGAGC TAGAACGTGT CAAAGCATTA      900
GGCGTGAAGC CCCCCCAGAA TCTCTGGGAA TATAAGGCTG TGAACCCAGG CAGGTCCCTG      960
TTCCTGCTAT ACGCCCTCAA GAGCTCCCCC AGGCTGAGTC TGCTCTACCT GTACCTGTTT     1020
GACTACACCG ACACCTTCCT ACCTTTCATC CACACCATCT GCCCTCTGCA AGAAGACAGC     1080
TCTGGGGAGG ACATCGTCAC CAAGCTTCTG GATCTTAAGG AGCCTACGTG GAAGCAGTGG     1140
AGAGAGTTCC TGGTCAAATA CTCCTTCCTT CCATACCAGC TGATTGCTGA GTTTGCTTGG     1200
GACTGGTTGG AGGTCCATTA CTGGACATCA CGGTTTCTCA TCATCAATGC TATGTTACTC     1260
TCAGTTCTGG AATTATTCTC CTTTTGGAGA ATCTGGTCGA GAAGTGAACT GAAGACCGTG     1320
CCTCAGAGGA TGTGGAGCCA TTTCTGGAAA GTATCAACGC AGGGACTTTT TGTGGCCATG     1380
TTCTGGCCCC TCATCCCTCA GTTTGTTTGC AACTGTTTGT TTTACTGGGC CCTGTACTTT     1440
AACCCAATTA TTAACATTGA TCTTGTGGTC AAGGAACTCC GGCGGCTGGA AACCCAGGTG     1500
TTGTGACTGG CACTGCCCAG GCTGAGACTC TTCAAGTCCC GCTGACGTCT GAGCTTTGAT     1560
GCTTAAGAAG GGTGAGGCAG GGAGCGGACT TCTTATTTTC AACCTTCAGT AAAACAAGGT     1620
GTTGCTTTGT ATATCAAAAG CTCCAACCAT GTCTTTTCCC CTTCAGCCTG TGGGTGGCAC     1680
GAGCAAGGAC TGACATCCGC ACAGGGAGGA TTGTCTGTTT GGCTGACACA GCAGCAGCCT     1740
TTCCCACCCA GCCACTTTCT TCACAGGGAT TAGGAGGCTC AGTCCCCAAC GGCTGGCAAG     1800
ACTCAGGGTC CTCAGTGGAC ATGGTGTGGG TGACATCAGA AGGGTGCCAC ATCAGTCCCC     1860
TCCCCAACCT CAGTGACTGA CAGAGGATCC GGATCTCAGA GCCTGAGACC AGGTTTATTG     1920
GGGCCTGGCC TGTCCTCTAA GTCAAGTTTA GGAAAACAAG GATAAGATTC TGTCATAGGC     1980
ATAGAGAGTT GCACATAAAA AATACCGAAG AAAACCCAAA ATTCAATCAA CAATTCTGTC     2040
TTATTGAAGA GTTGCTAGGA TTCAGAGTAA AACTCAAAGG ATTCAGTTTG AGCCTAGAAT     2100
GATGGTTAGA CTTGTAGTCA CTGGGCTTTT GTTTTGCTTT ATGGAAATCA TTGAAGGTCT     2160
GGATCCCTTT CTCTGAATGG AGAGATTGAG AGGGATGTCG GGCAGTTCCC ATTAGATTTA     2220
GTGGCCTTCA TGTTATTCAG AATTGTTTTG GTGATACCTC ACCCCTGTAA TCCCAGCACT     2280
TTGGGTGGGT GAGGCAGGCG GATCACTTGA AGCCAGGACT TCAAGACCAG CTTGGCCAAC     2340
ATGGTGAAAC CTCATCTCTA CTAAAAATAC AAAAATTAGC CAAGTGTGAT GGCACATACC     2400
TGTAATCCCA GCTACTTGGA ATTGGAAATC GCCTGAACCC AGGAGGCGGA GGTTGCAGGG     2460
AGGGAGACTG CACCACTGCA CTTCAGCCTG GGTGACAGAG GGAGACTCTG TCTTAAAAAA     2520
```

AAAAAAAAAA A                                                                                 2531

(2) INFORMATION FOR SEQ ID NO: 5:

(i) SEQUENCE CHARACTERISTICS:
        (A) LENGTH: 2531 base pairs
        (B) TYPE: nucleic acid
        (C) STRANDEDNESS: single
        (D) TOPOLOGY: linear (xi) SEQUENCE DESCRIPTION: SEQ ID NO: 5:

```
TTTTTTTTTT TTTTTTTAAG ACAGAGTCTC CCTCTGTCAC CCAGGCTGAA GTGCAGTGGT      60
GCAGTCTCCC TCCCTGCAAC CTCCGCCTCC TGGGTTCAGG CGATTTCCAA TTCCAAGTAG     120
CTGGGATTAC AGGTATGTGC CATCACACTT GGCTAATTTT TGTATTTTTA GTAGAGATGA     180
GGTTTCACCA TGTTGGCCAA GCTGGTCTTG AAGTCCTGGC TTCAAGTGAT CCGCCTGCCT     240
CACCCACCCA AAGTGCTGGG ATTACAGGGG TGAGGTATCA CCAAAACAAT TCTGAATAAC     300
ATGAAGGCCA CTAAATCTAA TGGGAACTGC CCGACATCCC TCTCAATCTC TCCATTCAGA     360
GAAAGGGATC CAGACCTTCA ATGATTTCCA TAAAGCAAAA CAAAAGCCCA GTGACTACAA     420
GTCTAACCAT CATTCTAGGC TCAAACTGAA TCCTTTGAGT TTTACTCTGA ATCCTAGCAA     480
CTCTTCAATA AGACAGAATT GTTGATTGAA TTTTGGGTTT TCTTCGGTAT TTTTTATGTG     540
CAACTCTCTA TGCCTATGAC AGAATCTTAT CCTTGTTTTC CTAAACTTGA CTTAGAGGAC     600
AGGCCAGGCC CCAATAAACC TGGTCTCAGG CTCTGAGATC CGGATCCTCT GTCAGTCACT     660
GAGGTTGGGG AGGGGACTGA TGTGGCACCC TTCTGATGTC ACCCACACCA TGTCCACTGA     720
GGACCCTGAG TCTTGCCAGC CGTTGGGGAC TGAGCCTCCT AATCCCTGTG AAGAAAGTGG     780
CTGGGTGGGA AAGGCTGCTG CTGTGTCAGC CAAACAGACA ATCCTCCCTG TGCGGATGTC     840
AGTCCTTGCT CGTGCCACCC ACAGGCTGAA GGGGAAAAGA CATGGTTGGA GCTTTTGATA     900
TACAAAGCAA CACCTTGTTT TACTGAAGGT TGAAAATAAG AAGTCCGCTC CCTGCCTCAC     960
CCTTCTTAAG CATCAAAGCT CAGACGTCAG CGGGACTTGA AGAGTCTCAG CCTGGGCAGT    1020
GCCAGTCACA ACACCTGGGT TTCCAGCCGC CGGAGTTCCT TGACCACAAG ATCAATGTTA    1080
ATAATTGGGT TAAAGTACAG GGCCCAGTAA AACAAACAGT TGCAAACAAA CTGAGGGATG    1140
AGGGGCCAGA ACATGGCCAC AAAAAGTCCC TGCGTTGATA CTTTCCAGAA ATGGCTCCAC    1200
ATCCTCTGAG GCACGGTCTT CAGTTCACTT CTCGACCAGA TTCTCCAAAA GGAGAATAAT    1260
TCCAGAACTG AGAGTAACAT AGCATTGATG ATGAGAAACC GTGATGTCCA GTAATGGACC    1320
TCCAACCAGT CCCAAGCAAA CTCAGCAATC AGCTGGTATG GAAGGAAGGA GTATTTGACC    1380
AGGAACTCTC TCCACTGCTT CCACGTAGGC TCCTTAAGAT CCAGAAGCTT GGTGACGATG    1440
TCCTCCCCAG AGCTGTCTTC TTGCAGAGGG CAGATGGTGT GGATGAAAGG TAGGAAGGTG    1500
TCGGTGTAGT CAAACAGGTA CAGGTAGAGC AGACTCAGCC TGGGGAGCT CTTGAGGGCG     1560
TATAGCAGGA ACAGGGACCT GCCTGGGTTC ACAGCCTTAT ATTCCCAGAG ATTCTGGGGG    1620
GGCTTCACGC CTAATGCTTT GACACGTTCT AGCTCCATGA GGATGGCTCT CCTGTGGCTG    1680
CTGTTTTCTA TGGTATAGGG CGTCTTGGAA AATTCTTCCT CTGTCAAAGT TAAAAGCAAC    1740
CTTCCATTTA CTCGTTCAGA TAAAAACCTT TCCCTGTAAA GAGATGCCCA AGGGCCCAGC    1800
TGCTCCAGCC AGAGGACAAC TTCTTCCGCC GTCCATTTGG CCACAGCCTT GTGGACCAGG    1860
AGGTCGTGTT CAGATTCCCT GCTGCTCCAG TGATAGACGA GCAGGACCAC TGCCACTCCA    1920
GTTAAAGCTG TGAGCACACC GGAAAAGAAT CCCCCTCCCA TCTGCTGATT CGCTCGGCCT    1980
```

```
GTGTTAGGAG CTAAAGGAAT CTGATCATTC CCATATTTCT GAAAGGCTGC AAGACTTTGG    2040

ACTATGTCAT TATTCTGCTG AATGTCTTCA AATCTCAGTC TAATGGCATC AGGAAATAAC    2100

TTTTCAATGG CATCCCTGAG GAGAATACTG ACTTTGGGGA AACCTTCCCA TTTTTCTCTG    2160

CATTCTGGAC ATTCTGTTTT CTTTGAAGAT GCCCACCATA AAGCAAGGCA GTGACGGCAG    2220

AAGCTGTGCC CACAGTTCAA GGTGGTGGGG TTAACCAGGA TGTCGTAGCA GCAGTGGCAA    2280

GAAAATTCAC TAACAGAAAT CTGAGGGCCG GTGCTTTTGA GAGGTTCATC TCTCTCAAGG    2340

TCCATTGTGT TCACATAGCT TTTCTGAGGT TCCTCCATCT CTTAGCAAAT TCTGGGTTCC    2400

AGAGACATAA AAAATTTCAG ACGTAGAAAA CTGCTGCAAA ACATCATTAA TCATTCCACT    2460

CGTCCCGGGC CAACCGGGCC ATTATTCTCA GCACAGACCC CGCGGGAGCA GAGGAAGAGG    2520

GAGAGGCTTC G                                                       2531
```

(2) INFORMATION FOR SEQ ID NO: 6:

(i) SEQUENCE CHARACTERISTICS:
        (A) LENGTH: 450 amino acids
        (B) TYPE: amino acid
        (D) TOPOLOGY: linear (xi) SEQUENCE DESCRIPTION: SEQ ID NO: 6:

```
Met Glu Glu Pro Gln Lys Ser Tyr Val Asn Thr Met Asp Leu Glu Arg
 1               5                  10                  15

Asp Glu Pro Leu Lys Ser Thr Gly Pro Gln Ile Ser Val Ser Glu Phe
                20                  25                  30

Ser Cys His Cys Cys Tyr Asp Ile Leu Val Asn Pro Thr Thr Leu Asn
            35                  40                  45

Cys Gly His Ser Phe Cys Arg His Cys Leu Ala Leu Trp Trp Ala Ser
    50                  55                  60

Ser Lys Lys Thr Glu Cys Pro Glu Cys Arg Glu Lys Trp Glu Gly Phe
65                  70                  75                  80

Pro Lys Val Ser Ile Leu Leu Arg Asp Ala Ile Glu Lys Leu Phe Pro
                85                  90                  95

Asp Ala Ile Arg Leu Arg Phe Glu Asp Ile Gln Gln Asn Asn Asp Ile
                100                 105                 110

Val Gln Ser Leu Ala Ala Phe Gln Lys Tyr Gly Asn Asp Gln Ile Pro
            115                 120                 125

Leu Ala Pro Asn Thr Gly Arg Ala Asn Gln Gln Met Gly Gly Gly Phe
130                 135                 140

Phe Ser Gly Val Leu Thr Ala Leu Thr Gly Val Ala Val Leu Leu
145                 150                 155                 160

Val Tyr His Trp Ser Ser Arg Glu Ser Glu His Asp Leu Leu Val His
                165                 170                 175

Lys Ala Val Ala Lys Trp Thr Ala Glu Glu Val Leu Trp Leu Glu
                180                 185                 190

Gln Leu Gly Pro Trp Ala Ser Leu Tyr Arg Glu Arg Phe Leu Ser Glu
            195                 200                 205

Arg Val Asn Gly Arg Leu Leu Leu Thr Leu Thr Glu Glu Phe Ser
210                 215                 220

Lys Thr Pro Tyr Thr Ile Glu Asn Ser Ser His Arg Arg Ala Ile Leu
225                 230                 235                 240

Met Glu Leu Glu Arg Val Lys Ala Leu Gly Val Lys Pro Pro Gln Asn
                245                 250                 255

Leu Trp Glu Tyr Lys Ala Val Asn Pro Gly Arg Ser Leu Phe Leu Leu
```

-continued

```
                    260                 265                 270
Tyr Ala Leu Lys Ser Ser Pro Arg Leu Ser Leu Tyr Leu Tyr Leu
            275                 280                 285
Phe Asp Tyr Thr Asp Thr Phe Leu Pro Phe Ile His Thr Ile Cys Pro
    290                 295                 300
Leu Gln Glu Asp Ser Ser Gly Glu Asp Ile Val Thr Lys Leu Leu Asp
305                 310                 315                 320
Leu Lys Glu Pro Thr Trp Lys Gln Trp Arg Glu Phe Leu Val Lys Tyr
                325                 330                 335
Ser Phe Leu Pro Tyr Gln Leu Ile Ala Glu Phe Ala Trp Asp Trp Leu
            340                 345                 350
Glu Val His Tyr Trp Thr Ser Arg Phe Leu Ile Ile Asn Ala Met Leu
        355                 360                 365
Leu Ser Val Leu Glu Leu Phe Ser Phe Trp Arg Ile Trp Ser Arg Ser
370                 375                 380
Glu Leu Lys Thr Val Pro Gln Arg Met Trp Ser His Phe Trp Lys Val
385                 390                 395                 400
Ser Thr Gln Gly Leu Phe Val Ala Met Phe Trp Pro Leu Ile Pro Gln
                405                 410                 415
Phe Val Cys Asn Cys Leu Phe Tyr Trp Ala Leu Tyr Phe Asn Pro Ile
            420                 425                 430
Ile Asn Ile Asp Leu Val Val Lys Glu Leu Arg Arg Leu Glu Thr Gln
        435                 440                 445
Val Leu
    450

(2) INFORMATION FOR SEQ ID NO: 7:

(i) SEQUENCE CHARACTERISTICS:
        (A) LENGTH: 25 amino acids
        (B) TYPE: amino acid
        (D) TOPOLOGY: linear (xi) SEQUENCE DESCRIPTION: SEQ ID NO: 7:

Asp Arg Lys Ile Asn Phe Asp Ala Leu Leu Lys Phe Ser His Ile Thr
1               5                   10                  15
Pro Ser Thr Gln Gln His Leu Lys Lys
            20                  25

(2) INFORMATION FOR SEQ ID NO: 8:

(i) SEQUENCE CHARACTERISTICS:
        (A) LENGTH: 19 amino acids
        (B) TYPE: amino acid
        (D) TOPOLOGY: linear (xi) SEQUENCE DESCRIPTION: SEQ ID NO: 8:

Asp Leu Glu Arg Asp Glu Pro Leu Lys Ser Thr Gly Pro Gln Ile Ser
1               5                   10                  15
Val Ser Glu (2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 9:
```

GGGGATCCAT TTGGCCTTTC CAG                                              23

(2) INFORMATION FOR SEQ ID NO: 10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 10:

GGCTCGAGTT TTCTTCTCTT TCTTCTTATC C                                     31

(2) INFORMATION FOR SEQ ID NO: 11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 11:

GGGAATTCAA CATATTTGAT CGAAAGATC                                        29

(2) INFORMATION FOR SEQ ID NO: 12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 12:

GGCTCGAGTC ATTTCTTCTC TTTCTTCTT                                        29

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 13:

GGGAATTCAT GGAGGAACCT CAGAAAAGC                                        29

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 14:

GAAGATGCCC ACCATAAAGC A                                                21

(2) INFORMATION FOR SEQ ID NO: 15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 15:

```
CAGCACTGAC CCTTTTG                                                    17

(2) INFORMATION FOR SEQ ID NO: 16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 16:

AGCGGATAAC AATTTCACAC AGGA                                            24
```